(12) United States Patent
Del Soldato

(10) Patent No.: US 7,186,708 B2
(45) Date of Patent: Mar. 6, 2007

(54) STEROIDAL COMPOUNDS

(75) Inventor: Piero Del Soldato, Milan (IT)

(73) Assignee: Nicox S.A., Sophia Antipolis (FR)

( * ) Notice: Subject to any disclaimer, the term of this patent is extended or adjusted under 35 U.S.C. 154(b) by 65 days.

(21) Appl. No.: 11/028,198

(22) Filed: Jan. 4, 2005

(65) Prior Publication Data

US 2005/0176694 A1 Aug. 11, 2005

Related U.S. Application Data

(62) Division of application No. 09/926,327, filed as application No. PCT/EP00/03238 on Apr. 11, 2000, now Pat. No. 6,909,007.

(30) Foreign Application Priority Data

Apr. 13, 1999 (IT) ............... MI99A0751

(51) Int. Cl.
  *A61K 31/56* (2006.01)
  *C07J 5/00* (2006.01)
(52) U.S. Cl. .............. 514/179; 514/180; 552/570; 552/574
(58) Field of Classification Search .......... 552/570, 552/574; 514/179, 180
See application file for complete search history.

(56) References Cited

U.S. PATENT DOCUMENTS

| | | | |
|---|---|---|---|
| 3,702,335 | A | 11/1972 | Lafill |
| 3,963,707 | A | 6/1976 | Högberg et al. |
| 4,913,852 | A | 4/1990 | Milioni et al. |
| 4,956,384 | A | 9/1990 | Chiesi et al. |
| 5,318,987 | A | 6/1994 | Weithmann et al. |
| 5,508,275 | A | 4/1996 | Weithmann et al. |
| 5,707,984 | A | 1/1998 | Tjoeng et al. |
| 5,837,698 | A | 11/1998 | Tjoeng et al. |

FOREIGN PATENT DOCUMENTS

| | | |
|---|---|---|
| DE | 19634793 | 3/1998 |
| EP | 0 549 318 A2 | 6/1993 |
| EP | 0 562 497 A1 | 9/1993 |
| EP | 0 578 494 A1 | 1/1994 |
| JP | 58-045724 | 3/1983 |
| JP | 4-273892 | 9/1992 |
| JP | 5-39261 | 2/1993 |
| WO | WO 98/15568 | 4/1998 |

OTHER PUBLICATIONS

International Search Report; Nov. 21, 2000.
Hungarian Novelty Search Report; Mar. 23, 2004.
Cederqvist et al., *Biochem. Pharmacol.* 47(6), 1047-1053, 1994.
Bonn et al., *Cardiovasc. Drug Rev.* 16(3), 195-211, 1998.
K. B. Schwarz, "Oxodative Stress During Viral Infection: A Review", Free Radical Biology & Medicine, vol. 21, No. 5, 1996, pp. 641-649.
Goodman & Gillman, "The Pharmacological Basis of Therapeutics", 9th Edition, 1996, McGraw-Hill Health Preffsions Division, pp. 1459-1465 and 1474.
Martindale, The Extraphamacopeia, 30th Edition, 1993, pp. 712-723.
Nenseter et al, "Paracetamol nhibits Copper Ion-Induced, Azo Compound-Initialed, and Mononuclear Cell-Mediated Oxidative Modification of LDL", Arterioscierosis, Thombosis, and Vascular Biology, vol. 15, No. 9, Sep. 1995, pp. 1338-1344.
Baylis et al, "Chronic Blockade of Nitric Oxide Synthesis in the Rat Produces Syntemic Hypertension and Glomemerular Damage", J. Clin. Investigation, vol. 90, 1992, pp. 279-281.

*Primary Examiner*—Barbara P. Badio
(74) *Attorney, Agent, or Firm*—Arent Fox PLLC

(57) ABSTRACT

Steroidal compounds or their salts having general formula:

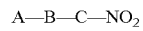

are described, wherein:
  A=R—, wherein R is a steroidal drug radical;
  B=—$T_B$—$X_2$—$T_{BI}$—, wherein $T_B$ is (CO), $T_{BI}$ is O, S, NH, and $X_2$ is a bivalent bridging group; and
  C is a bivalent radical.

8 Claims, No Drawings

STEROIDAL COMPOUNDS

The present application is a divisional of U.S. patent application Ser. No. 09/926,327, filed Oct. 15, 2001, now U.S. Pat. No. 6,909,007, which is a National Stage entry of PCT/EP00/03238, filed Apr. 11, 2000. All prior patent applications are hereby incorporated by reference in their entirety.

The present invention relates to novel steroidal compounds for systemic use and non systemic use, and their compositions, to be used in the conditions of oxidative stress and/or endothelial dysfuntions. Specifically it relates to compounds with a steroidal structure having antiinflammatory, immunodepressive and angiostatic activity (the so called antiinflammatory steroids), or gastrointestinal activity.

The compounds according to the present invention result therapeutically useful in the treatment of morbid conditions wherein the steroidal products are generally used with greater benefit, in terms both of a better tolerability and/or efficacy.

By oxidative stress it is meant the generation of free radicals on radicalic compounds, which causes injury both of the cell and of that of the surrounding tissue (Pathophysiology: the biological basis for disease in adults and children, McCance & Huether 1998 pages 48–54).

By endothelial dysfunctions are meant those relating to the vasal endothelium. The damage of the vasal endothelium is known as one of those important events that can bring about a series of pathological processes affecting various organs and body apparatuses, as described hereinafter (Pathophysiology: The biological basis for disease in adults and children, McCance & Huether 1998 page 1025).

As known, the oxidative stress and/or the endothelial dysfunctions are associated to various pathologies as reported hereinafter. The oxidative stress can also be caused by toxicity of a great variety of drugs, which significantly affects their performances.

Said pathological events are of a chronic, debilitating character and are very of then typical of the elderly. As already said, in said pathological conditions the drugs used show a remarkably worsened performance.

Examples of pathological situations caused by the oxidative stress and/or by the endothelial dysfunctions, or present in elderly, are the following:

For the cardiovascular system: myocardial and vascular ischaemia in general, hypertension, stroke, arteriosclerosis, etc.
For the connective tissue: rheumatoid arthritis and connected inflammatory diseases, etc.
For the pulmonary system: asthma and connected inflammatory diseases, etc.
For the gastrointestinal system: ulcerative and non ulcerative dyspepsias, intestinal inflammatory diseases, etc.
For the central nervous system: Alzheimer disease, etc.
For the urogenital system: impotence, incontinence.
For the cutaneous system: eczema, neurodermatitis, acne.
The infective diseases in general (ref.: Schwarz-KB, Brady "Oxidative stress during viral infection: A review" Free radical Biol. Med. 21/5, 641–649 1996).

Further the ageing process can be considered as a true pathologic condition (ref. Pathophysiology: the biological basis for disease in adults and children, pages 71–77).

The known drugs when administered to patients having pathologies associated to oxidative stress and/or endothelial dysfunctions, show a lower efficacy and/or higher toxicity. This happenss for example with steroids.

Drug research is directed to find new molecules having an improved therapeutic index (efficacy/toxicity ratio) or a lower risk/benefit ratio, also for pathological conditions as those above mentioned, wherein the therapeutic index of a great number of drugs results lowered. In fact in the above mentioned conditions of oxidative stress and/or endothelial dysfunctions, many drugs show a lower activity and/or higher toxicity.

It is well known that steroids represent a first choice pharmacological intervention in the therapy of inflammatory diseases. This class of drugs, among which can be mentioned for example hydrocortisone, cortisone, prednisone, prednisolone, fludrocortisone, desoxycorticosterone, metilprednisolone, triamcinolone, paramethasone, betamethasone, dexamethasone, triamcinolone acetonide, fluocinolone acetonide, beclomethasone, acetoxypregnelone, etc., elicits remarkable pharmaco-toxicological effects on different organs, and for this reason both their clinical use and its interruption cause a series of side effects, some of which very serious. See for example Goodman & Gilman, "The pharmaceutical Basis of Therapeutics" $9^{th}$ ed., pages 1459–1465, 1996.

Among said toxic effects can be mentioned those affecting the bone tissue leading to an altered cellular metabolism and an high osteoporosis incidence; those affecting the cardiovascular system, generating an hypertensive response; those affecting the gastrointestinal apparatus giving gastric damages.

See for example Martindale "The extrapharmacopoeia", $30^{th}$ ed., pages 712–723, 1993.

To the class of steroidal drugs belong also biliary acids, that have been used in the therapy of hepatic disorders and in biliary colics. Ursodesoxycholic acid is also used in some hepatic dysfunctions (hepatic cirrhosis of biliary origin, etc.). Their tolerability is strongly worsened in the presence of gastrointestinal complications (chronic hepatic damage, peptic ulcer, intestinal inflammation, etc.). Also in the case of biliary acids the oxidative stress remarkably affects drug performance: both the efficacy and the tolerability of chenodeoxycholic, and ursodesoxycholic acids are significantly reduced. In particular the unwanted effects on liver are found exalted. Among the steroidal compounds can be mentioned also estrogens for the treatment of dislipidaemias, hormonal troubles, female apparatus tumours treatment can be mentioned. Also said steroids show side effects as above mentioned, in particular at the hepatic level.

According to the above mentioned prior art it seems almost impossible to separate therapeutic activity from side effects, see Goodman et al, above mentioned, at p. 1474.

The steroidal compounds are completely different from the antiinflammatory non steroidal compounds from the chemical, pharmacological and biochemical point of view, since the pharmaco-toxicological mechanism of action of nonsteroidal antiinflammatory products is based on the inhibition of one or more of the cyclooxygenases (COX), while steroids do not influence COX and have more complex pharmaco-toxicological mechanisms of action not yet fully cleared.

Indeed it is well known that these two groups of drugs are classified in different classes in the pharmacopoeias.

The need was felt to have available steroids showing an improved therapeutic performance, i.e. endowed both of a lower toxicity and/or higher efficacy, so that they could be administered to patients in morbid conditions of oxidative stress and/or endothelial dysfunctions, without showing the drawbacks of the drugs of the prior art.

It has been now surprisingly and unexpectedly found that the aforementioned technical problems shown in the administration of steroidal drugs to patients affected by oxidative stress and/or endothelial dysfunctions, or to the elderly in general, are solved by a new class of drugs as described hereinafter.

An object of the invention are steroidal compounds or their salts having the following general formulas (I) and (II):

$$A—(B)_{b0}—C—N(O)_s \quad (I)$$

wherein:
s=is an integer equal to 1 or 2, preferably s=2;
b0=0 or 1;
A=R—$T_1$—, wherein R is the steroidal drug radical as defined hereunder,
B=—$T_B$—$X_2$—$T_{BI}$— wherein
  $T_B$ and $T_{BI}$ are equal or different;
  $T_B$=(CO) when the reactive function in the precursor steroid is —OH; $T_B$=X when the reactive function in the precursor steroid is —COOH;
  X=O, S, $NR_{1C}$, $R_{1C}$ is H or a linear or branched alkyl having from 1 to 5 carbon atoms, or a free valence;
  $T_{BI}$=(CO)$_{tx}$ or (X)$_{txx}$, wherein tx and txx have the value of 0 or 1; with the proviso that tx=1 when txx=0, tx=0 when txx=1; X is as above defined;
  $X_2$ is a bivalent bridging bond as defined hereunder;
C is the bivalent radical —$T_C$—Y— wherein
  $T_C$=(CO) when tx=0, $T_C$=X when txx=0, X being as above defined;
Y is:

$$—[C]_{nIX}\genfrac{}{}{0pt}{}{R_{TIX}}{R_{TIX'}}—Y^3—[C]_{nIIX}\genfrac{}{}{0pt}{}{R_{TIIX}}{R_{TIIX'}}—O— \quad (III)$$

wherein:
  nIX is an integer between 0 and 3, preferably 1;
  nIIX is an integer between 1 and 3, preferably 1;
  $R_{TIX}$, $R^{TIX'}$, $R^{TIIX'}$, equal to or different from each other are H or a linear or branched $C_1$–$C_4$ alkyl; preferably $R_{TIX}$, $R_{TIX'}$, $R_{TIIX}$, $R_{TIIX'}$ are H.
  $Y^3$ is a saturated, unsaturated or aromatic heterocyclic ring containing at least one nitrogen atom, preferably one or two nitrogen atoms, said ring having 5 or 6 atoms.
or Y is $Y_0$, selected from the following:
  an alkylenoxy group R'O wherein R' is linear or branched when possible $C_1$–$C_{20}$, preferably having from 1 to 6 carbon atoms, most preferably 2–4 carbon atoms, or a cycloalkylene having from 5 to 7 carbon atoms, in the cycloalkylenic ring one or more carbon atoms can be substituted with heteroatoms, the ring can have side chains of R' type, R' being as above defined; or —(CH$_2$)$_{n3}$—[benzene ring]—(CH$_2$)$_{n3'}$—O— wherein n3 is an integer from 0 to 3 and n3' is an integer from 1 to 3;

[benzene ring with COOH and (CH$_2$)$_{n3}$ and (CH$_2$)$_{n3'}$—O—]

wherein n3 and n3' have the above mentioned meaning

—(CH$_2$—CH(ONO$_2$)—CH$_2$—O)$_{nf'}$—

—(CH$_2$—CH(ONO$_2$)—CH$_2$—O)$_{nf'}$— wherein nf' is an integer from 1 to 6 preferably from 1 to 4;

—(CH(R$_{1f}$)—CH$_2$—O)$_{nf}$—    —(CH$_2$—CH(R$_{1f}$)—O)$_{nf}$— wherein $R_{1f}$=H, CH$_3$ and nf is an integer from 1 to 6; preferably from 1 to 4;

preferably Y=—$Y_0$=R'O— wherein R' is as above defined;
preferably R' is a $C_1$–$C_6$ alkylene;

$$A—C_1—B_1 \atop |\; N(O)_s \quad (II)$$

wherein:

$$C_1 = \;—T_{CI}—Y'—T_{CII}—$$

wherein $T_{CI}$ and $T_{CII}$ are equal or different,
$T_{CI}$=(CO) when the reactive function of the precursor steroid is —OH, $T_{CI}$=X when the reactive function of the precursor steroid is —COOH, X being as above defined;
$T_{CII}$=(CO)$_{tI}$ or (X)$_{tII}$, wherein tI and tII have the 0 or 1 value; with the proviso that tI=1 when tII=0; tI=0 when tII=1; X is as above defined;
Y' is as Y above defined, but with three free valences instead of two, preferably it is selected from the following:
  a —R'O— group wherein R' is linear or branched $C_1$–$C_{20}$, preferably having from 1 to 6 carbon atoms, most preferably 2–4, or a saturated, optionally substituted, ring having from 5 to 7 carbon atoms; or

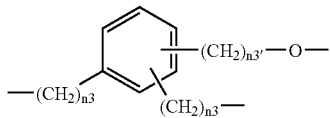

wherein n3 is an integer from 0 to 3 and n3' is an integer from 1 to 3;

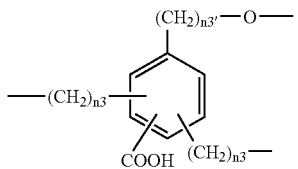

wherein n3 and n3' have the above mentioned meaning;

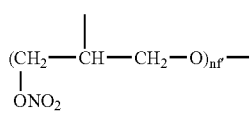

wherein one hydrogen atom on one of the carbon atoms is substituted by a free valence;

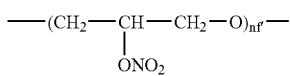

wherein nf' is an integer from 1 to 6 preferably from 1 to 4; wherein one hydrogen atom on one of the carbon atoms is substituted by a free valence;

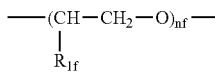

wherein one hydrogen atom on one of the carbon atoms is substituted by a free valence;

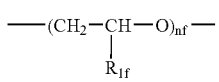

wherein $R_{1f}$=H, $CH_3$ and nf is an integer from 1 to 6; preferably from 1 to 4; wherein one hydrogen atom on one of the carbon atoms is substituted by a free valence;

preferably Y'=—R'O— wherein R' is a linear or branched $C_2$–$C_4$, the oxygen which in Y' is covalently linked to the —N(O)$_s$ group is at the end of the free bond indicated in $C_1$ formula;

or Y'=$Y_0$ as defined in (I) but with three free valences instead of 2;

$B_1$=—$T_{BII}$—$X_{2a}$ wherein $X_{2a}$ is a monovalent radical, $T_{BII}$=(CO) when tI=0, $T_{BII}$=X when tII=0, X being as above defined;

$X_2$, bivalent radical, is such that the corresponding precursor of B: —$T_3$—$X_2$—$_{T3I}$— meets test 4 or test 5, precursor in which the $T_B$ and $T_{BI}$ free valences are each saturated with OZ, with Z or with

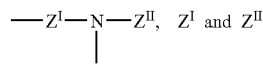

being equal or different and have the Z values as above defined, depending on whether $T_3$ and/or $T_{BI}$=CO or X, in connection with the values of t, t', tx and txx;

the C precursor when b0=0 is of —$T_C$—Y—H type wherein the $T_C$ free valence is saturated with OZ, Z, or with

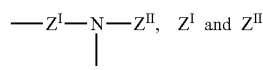

being as above defined and is such as to meet test 5;

$X_{2a}$ monovalent radical, such that the corresponding precursor of $B_1$—$T_{BII}$—$X_{2a}$ meets test 4 or test 5, precursor wherein the $T_{BII}$ free valence is saturated with OZ or with Z or with

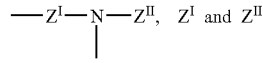

being equal or different and having the Z values as above defined depending on whether $T_{BII}$=CO or X, in connection with the tI and tII values;

A=R—, has the following structure:

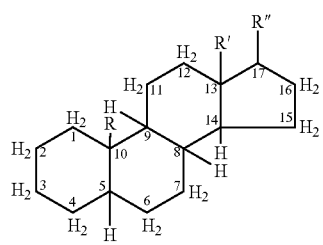

wherein in substitution of the hydrogens of the CH groups or of the two hydrogens of the $CH_2$ groups mentioned in the general formula, the following substituents can be present:

in position 1–2: there may be a double bond;

in position 2–3: there may be the following substituent:

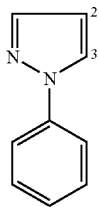

in position 2: there may be Cl, Br;
in position 3: there may be CO, —O—CH$_2$—CH$_2$—Cl, OH;
in position 3–4: there may be a double bond;
in position 4–5: there may be a double bond;
in position 5–6: there may be a double bond;
in position 5–10: there may be a double bond;
in position 6: there may be Cl, F, CH$_3$, —CHO;
in position 7: there may be Cl, OH;
in position 9: thre may be Cl, F;
in position 11: there may be OH, CO, Cl, CH$_3$;
in position 16: there may be CH$_3$, OH, =CH$_2$:
in position 17: there may be OH, CH$_3$, OCO(O)$_{ua}$(CH$_2$)$_{va}$ CH$_3$, C≡CH or

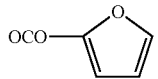

wherein ua is an integer equal to 0 or 1, va is an integer from 0 to 4;
in position 16–17: there may be the following groups:

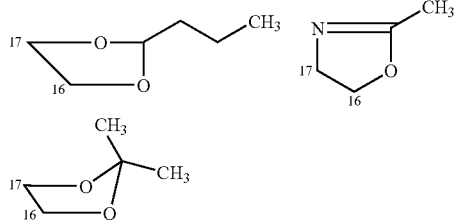

R and R', equal to or different from each other, can be hydrogen or linear or branched alkyls from 1 to 4 carbon atoms, preferably R=R'=CH$_3$;
R" is —(CO—L)$_t$—(L)$_{t2}$—(X$_O^I$)$_{t1}$—
wherein t, t1 and t2 are integers equal to or different from each other, equal to 0 or 1, with the proviso that when t=0 t2=1 and when t=1 t2=0, and that t and t1, or t2 and t1, cannot contemporaneously be equal to 0 when A does not contain —OH groups;
the bivalent bridging group L is selected from:

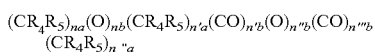

wherein na, n'a, and n"a, equal to or different from each other, are integers from 0 to 6, preferably 1–3; nb, n'b, n"b and n'"b, equal to or different from each other, are integers equal to 0 or 1; R$_4$, R$_5$, equal to or different from each other, are selected from H, linear or branched alkyl from 1 to 5 carbon atoms, preferably from 1 to 3;

X$_O^I$ is X as above defined, but R$_{1C}$ is a linear or branched alkyl from 1 to 10 carbon atoms, or equal to X$_2^I$ wherein X$_2^I$ is equal to —OH, CH$_3$, Cl, N(—CH$_2$—CH$_3$)$_2$, SCH$_2$F, SH, or

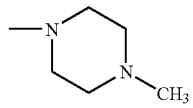

wherein test 4 is the following: it is an analytical determination carried out by adding portions of methanol solutions of the precursor of B or B$_1$ at a 10$^{-4}$ M concentration, to a methanol solution of DPPH (2,2-diphenyl-1-picryl hydrazyl free radical); after having maintained the solution at room temperature away from light for 30 minutes, it is read the absorbance at the wave length of 517 nm of the test solution and of a solution containing only DPPH in the same amount as in the test solution; and then the inhibition induced by the precursor towards radical production by DPPH is calculated as a percentage by means of the following formula:

$(1-A_S/A_C) \times 100$ wherein A$_S$ and A$_C$ are respectively the absorbance values of the solution containing the test compound+DPPH and that of the solution containing only DPPH; the acceptance criterium of the compounds according to this test is the following: test 4 is met by B or B$_1$ precursor compounds if the inhibition percentage as above defined is higher than or equal to 50%;
wherein test 5 is the following: it is an analytical determination carried out by adding aliquots of 10$^{-4}$ M methanol solutions of the precursor of B or B$_1$ or of C=—T$_C$—Y—H, having the free valence saturated as above indicated, to a solution formed by admixing a 2 mM solution of desoxyribose in water with 100 mM of phosphate buffer and 1 mM of the salt Fe$^{II}$ (NH$_4$)$_2$ (SO$_4$)$_2$; after having thermostatted the solution at 37° C. for one hour, aliquots of aqueous solutions of trichloroacetic acid 2.8% and of thiobarbituric acid 0.5 M are added, in the order, heating is effected at 100° C. for 15 minutes and the absorbance of the tested solutions is then read at 532 nm; the inhibition induced by the precursor of B or B$_1$ or C=—T$_C$—Y—H wish respect to radical production by Fe$^{II}$ is calculated as a percentage by means of the following formula:

$(1-A_S/A_C) \times 100$ wherein A$_S$ and A$_C$ are respectively the absorbance values of the solution containing the tested compound and the iron salt and that of the solution containing only the iron salt, the compound meets test 5 when the inhibition percentage as above defined of the precursor of B or B$_1$ or C=—T$_C$—Y—H, having the free valence saturated as above indicated, is higher than or equal to 50%; provided that in the compounds of formula (I) are excluded the drugs with A=R—, wherein R is as above defined, when b$_0$=0 and C=—T$_C$—Y$_0$— wherein the free valence of Y$_0$ is saturated as indicated above, s=1 or 2.

Preferably the B or B$_1$ precursor compound (precursor of the X$_2$ or X$_{2a}$ radical in formulas (I) and (II) respectively) which meets test 4, is selected from the following classes of compounds:

Aminoacids, selected from the following: L-carnosine (formula CI), anserine (CII), selenocysteine (CIII), selenomethionine (CIV), penicillamine (CV), N-acetyl-penicillamine (CVI), cysteine (CVII), N-acetylcysteine (CVIII), glutathione (CIX) or its esters, preferably ethyl or isopropyl ester:

hydroxyacids, selected from the following: gallic acid (formula DI), ferulic acid (DII), gentisic acid (DIII), citric acid (DIV), caffeic acid (DV), hydrocaffeic acid (DVI), p-coumaric acid (DVII), vanillic acid (DVIII), chlorogenic acid (DIX), kynurenic acid (DX), syringic acid (DXI):

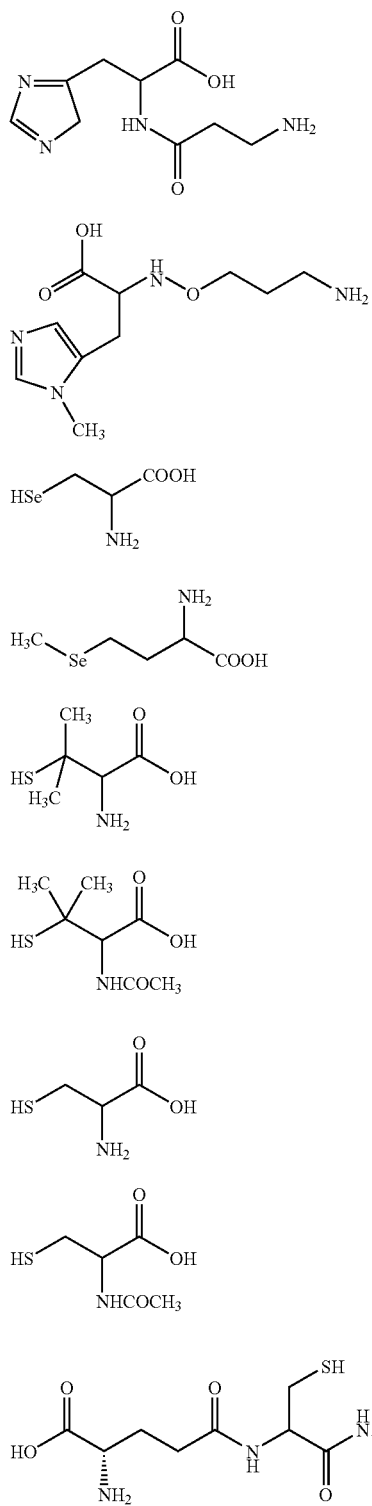
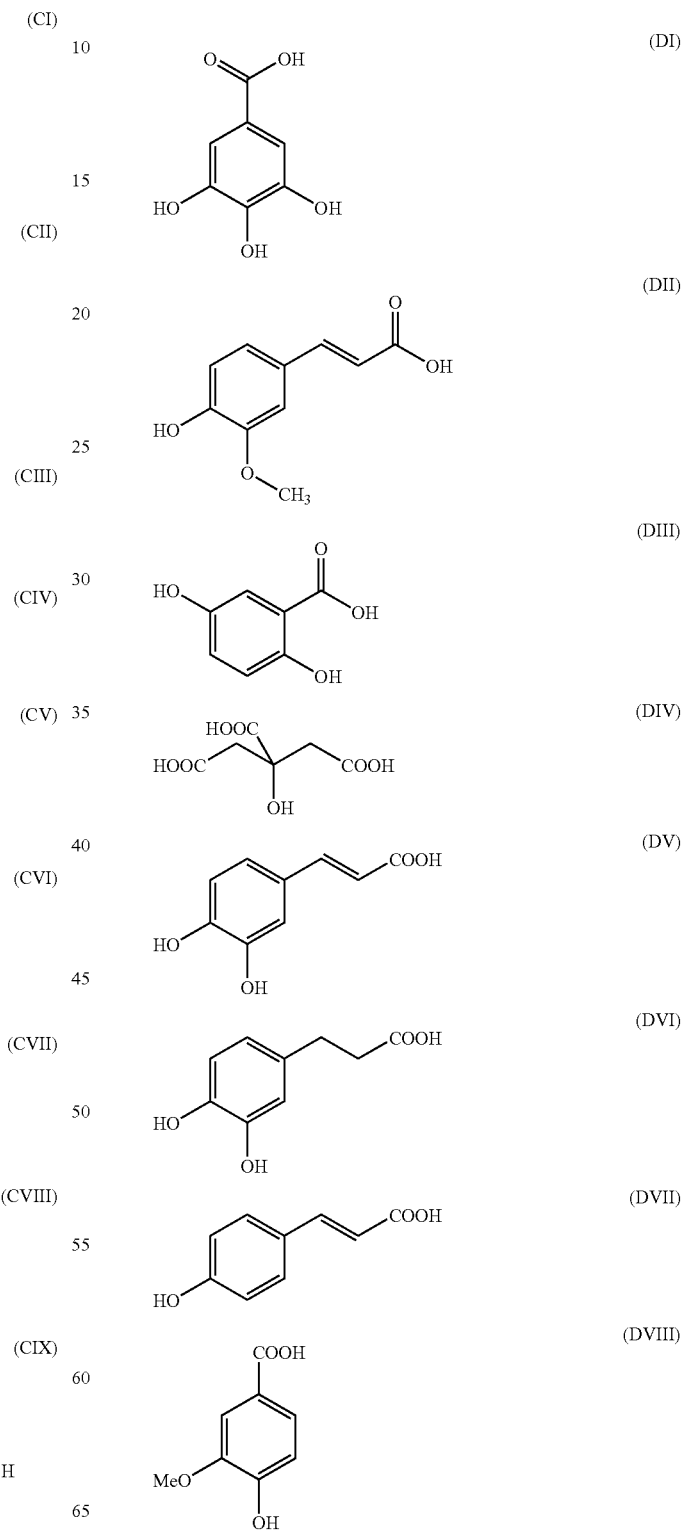

-continued

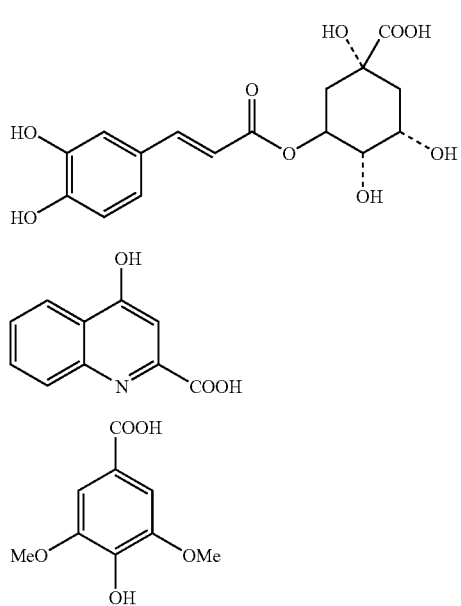

(DIX)

(DX)

(DXI)

Aromatic and heterocyclic mono- and polyalcohols, selected from the following: nordihydroguaiaretic acid (EI), quercetin (EII), catechin (EIII), kaempferol (EIV), sulphurethyne (EV), ascorbic acid (EVI), isoascorbic acid (EVII), hydroquinone (EVIII), gossypol (EIX), reductic acid (EX), methoxyhydroquinone (EXI), hydroxyhydroquinone (EXII), propyl gallate (EXIII), saccharose (EXIV), vitamin E (EXV), vitamin A (EXVI), 8-quinolol (EXVII), 3-tert-butyl-4-hydroxyanisole (EXVIII), 3-hydroxyflavone (EXIX), 3,5-tert-butyl-p-hydroxytoluene (EXX), p-tert-butyl phenol (EXXI), timolol (EXXII), xibornol (EXXIII), 3,5-di-ter-butyl-4-hydroxybenzyl-thioglycolate (EXXIV), 4'-hydroxybutyranilide (EXXV), guaiacol (EXXVI), tocol (EXXVII), isoeugenol (EXXVIII), eugenol (EXXIX), piperonyl alcohol (EXXX), allopurinol (EXXXI), conyferyl alcohol (EXXXII), 4-hydroxyphenetyl alcohol (EXXXIII), p-coumaric alcohol (EXXXIV), curcumin (EXXXV):

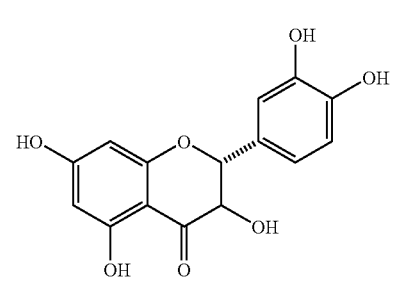

(EI)

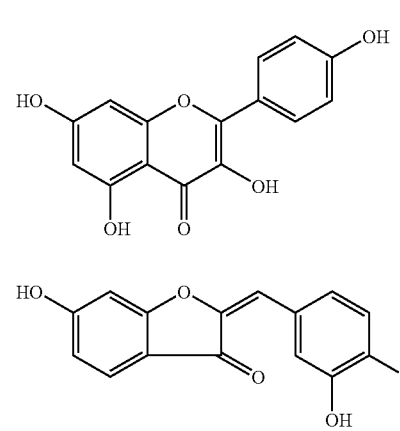

(EII)

(EIII)

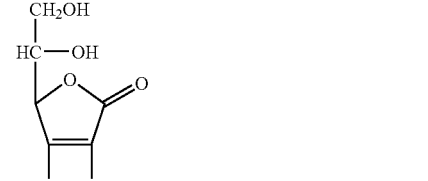

(EIV)

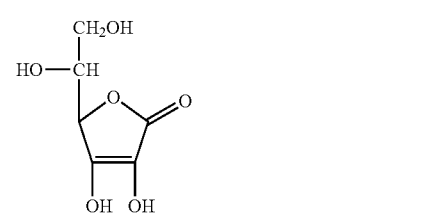

(EV)

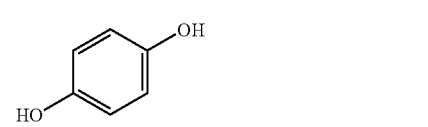

(EVI)

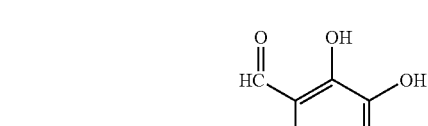

(EVII)

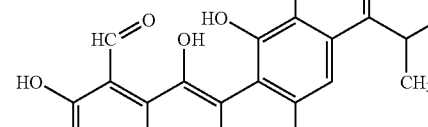

(EVIII)

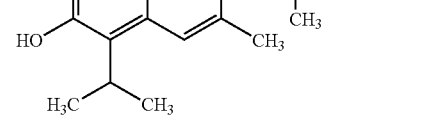

(EIX)

-continued
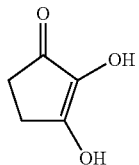
(EX)
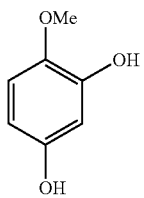
(EXI)
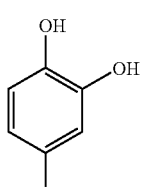
(EXII)
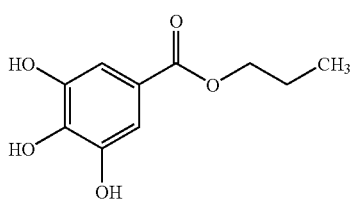
(EXIII)
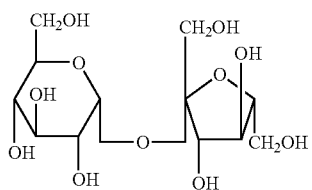
(EXIV)
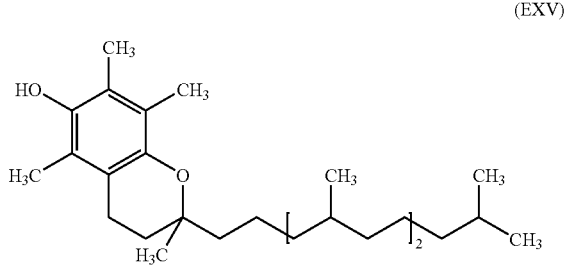
(EXV)
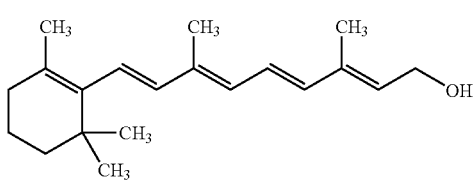
(EXVI)
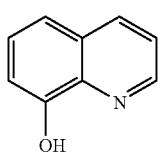
(EXVII)
-continued
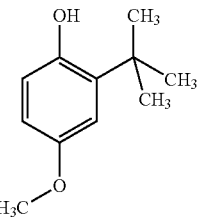
(EXVIII)
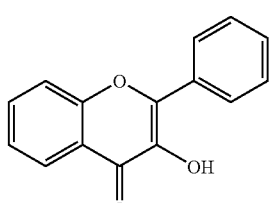
(EXIX)
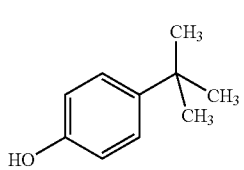
(EXXI)
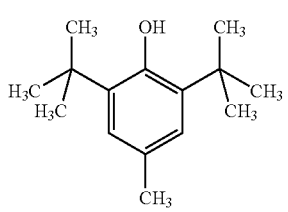
(EXX)
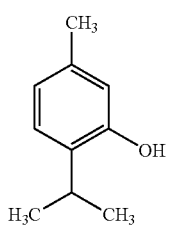
(EXXII)
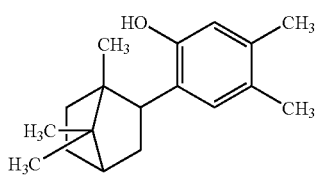
(EXXIII)
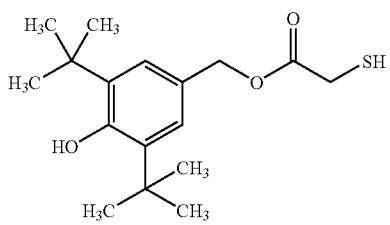
(EXXIV)
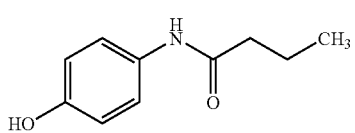
(EXXV)

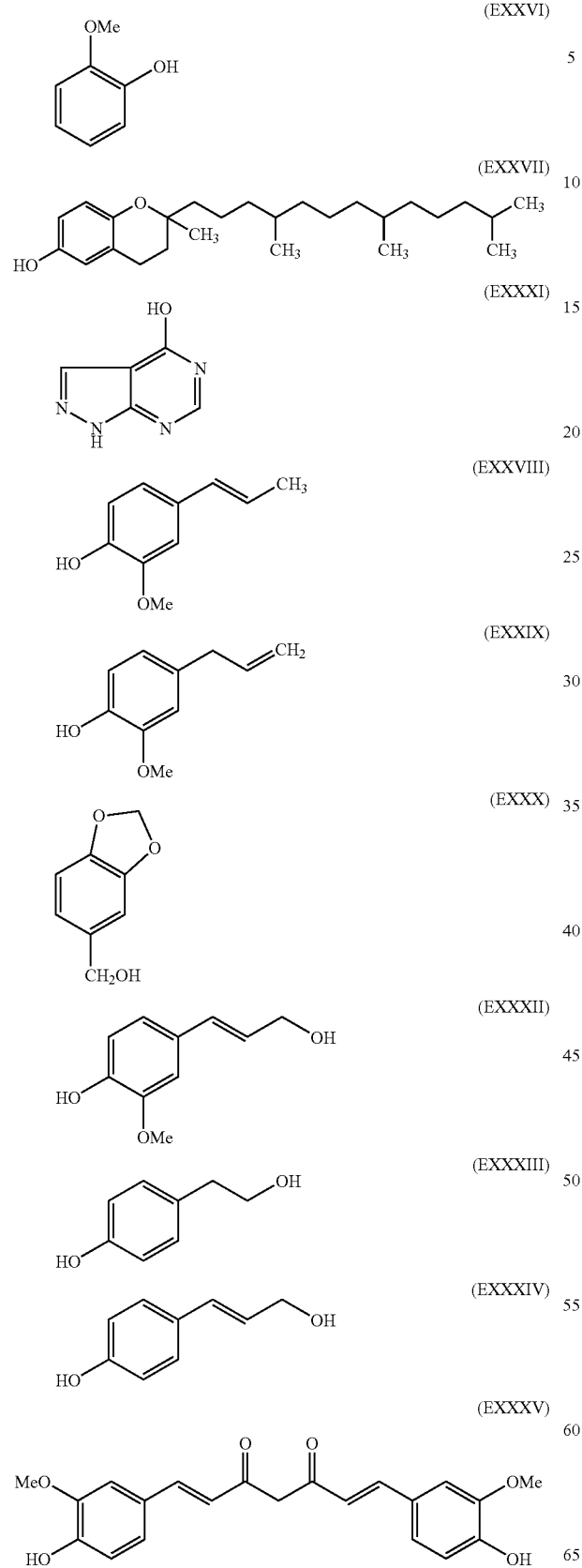

aromatic and heterocyclic amines, selected from the following: N,N'-diphenyl-p-phenylenediamine (MI), ethoxyquin (MII), thionine (MIII), hydroxyurea (MIV):

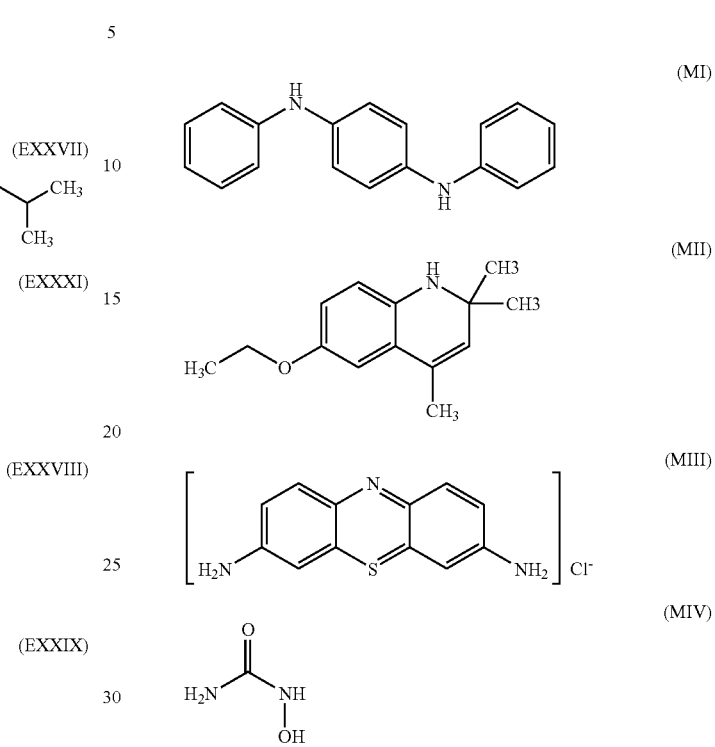

Compounds containing at least a free acid function, selected from the following: 3,3'-thiodipropionic acid (NI), fumaric acid (NII), dihydroxymaleic acid (NIII), thioctic acid (NIV), edetic acid (NV), bilirubin (NVI), 3,4-methylendioxycinnamic acid (NVII), piperonylic acid (NVIII):

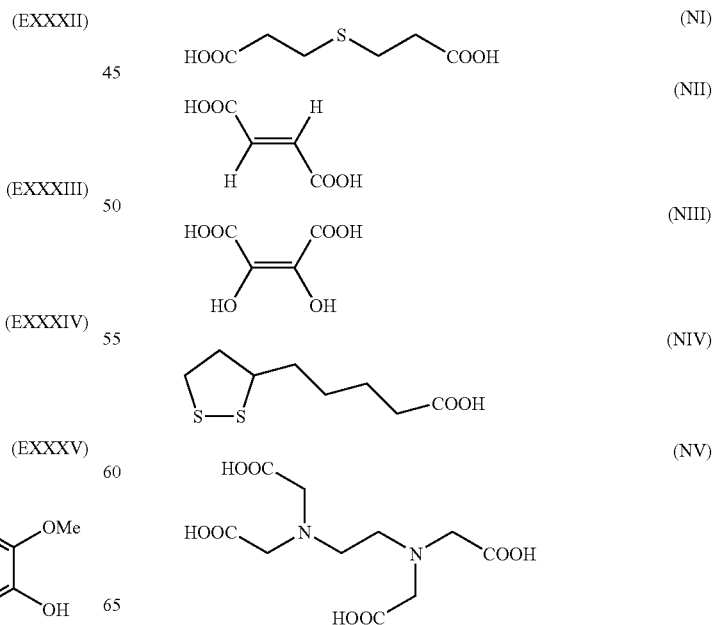

-continued

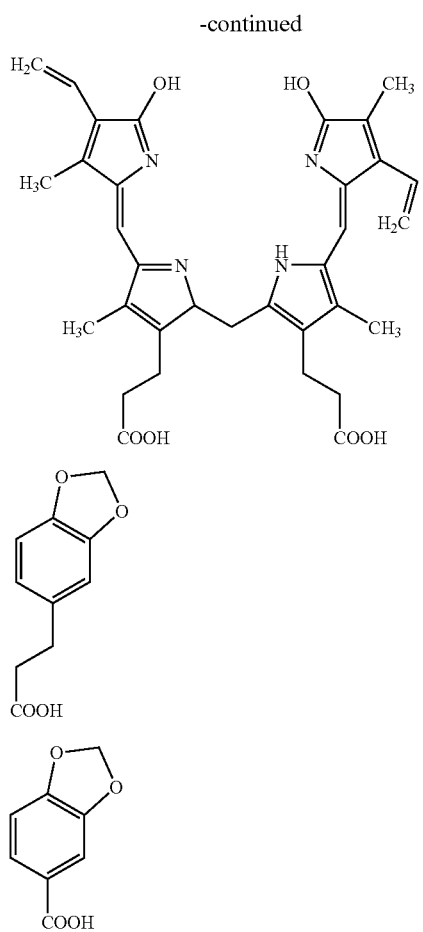

(NVI)

(NVII)

(NVIII)

The above mentioned substances precursors of B or B₁ are prepared according to the known methods in the prior art, described, for example, in "The Merck Index, 12a Ed. (1996), herein incorporated by reference. When available, the corresponding isomers and optical isomers can be used.

Preferably the precursor compound of B or of B₁ (precursor of the $X_2$ or $X_{2a}$ radical in formulas (I) and (II) respectively) which meets test 5, is selected from the following compounds:

Aminoacids: aspartic acid (PI), histidine (PII), 5-hydroxytryptophan (PIII), 4-thiazolidincarboxylic acid (PIV), 2-oxo-4-thiazolidincarboxylic acid (PV)

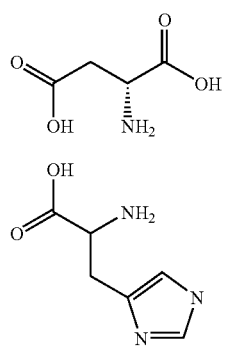

(PI)

(PII)

-continued

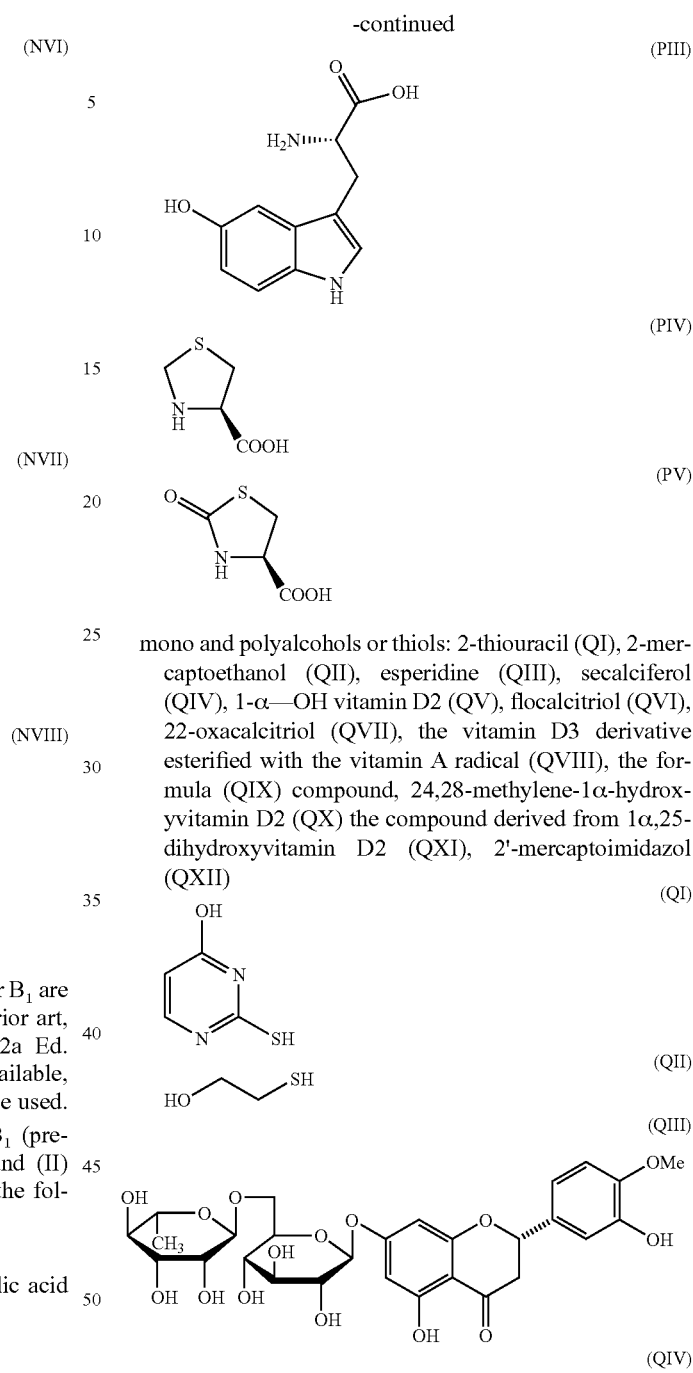

(PIII)

(PIV)

(PV)

mono and polyalcohols or thiols: 2-thiouracil (QI), 2-mercaptoethanol (QII), esperidine (QIII), secalciferol (QIV), 1-α—OH vitamin D2 (QV), flocalcitriol (QVI), 22-oxacalcitriol (QVII), the vitamin D3 derivative esterified with the vitamin A radical (QVIII), the formula (QIX) compound, 24,28-methylene-1α-hydroxyvitamin D2 (QX) the compound derived from 1α,25-dihydroxyvitamin D2 (QXI), 2'-mercaptoimidazol (QXII)

(QI)

(QII)

(QIII)

(QIV)

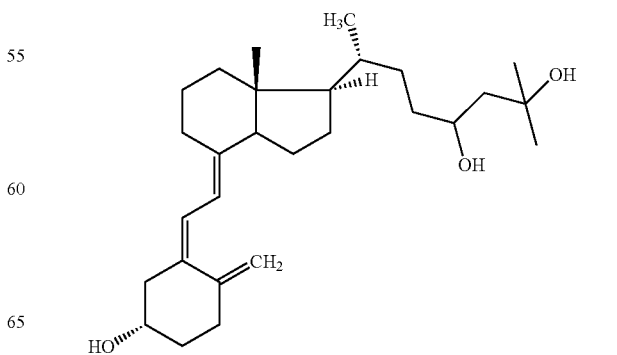

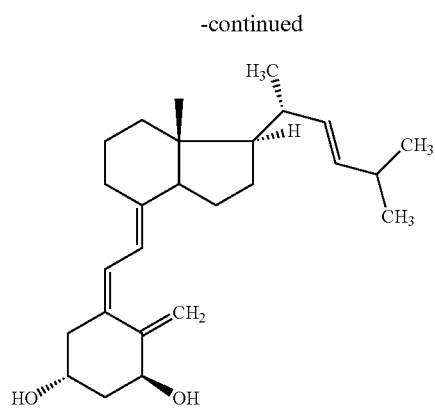
(QV)
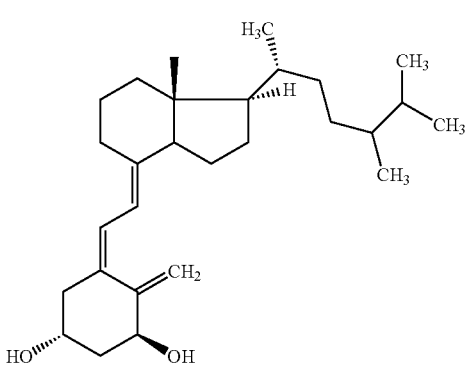
(QIX)
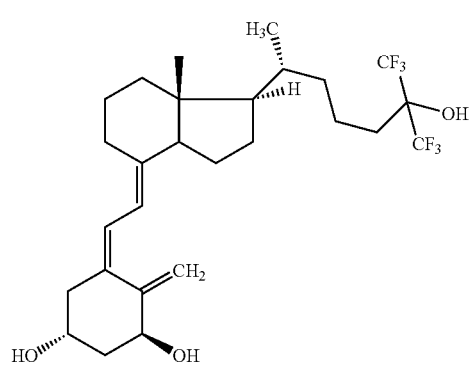
(QVI)
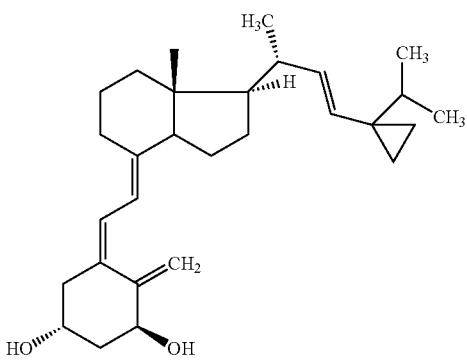
(QX)
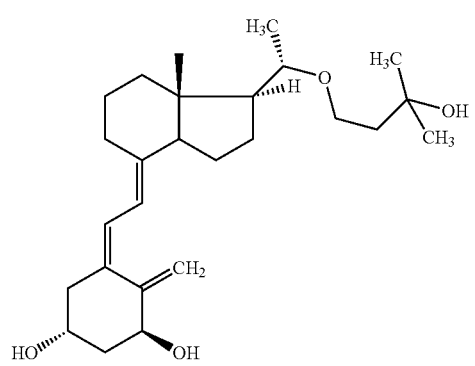
(QVII)
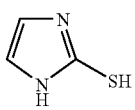
(QXII)
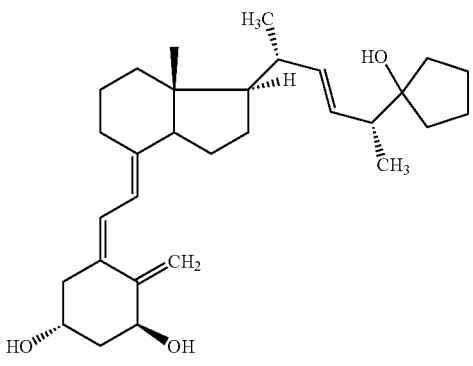
(QXI)
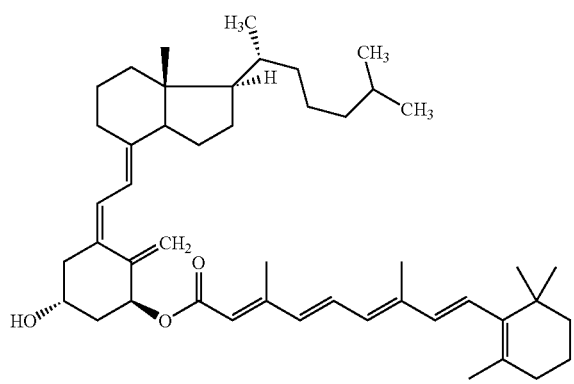
(QVIII)
(RI)
succinic acid
The precursor compounds of B or $B_1$ of the above mentioned groups P, Q and R are prepared according to the known methods in the prior art and described for example in "The Merck Index", $12^a$ Ed. (1996), herein incorporated by reference.

The vitamin D3 derivative with retinoic acid (QVIII) is prepared as described in JP 93039261 (ref. C.A. 119 117617); the formula (QIX) compound according to EP 562497; 24,28-methylene-1α-hydroxyvitamin D2 (QX) according to EP 578494; the derivative compound of dehydroxyvitamin D2 (QXI) according to EP 549,318.

The precursors of B or B$_1$ which meet test 4, are preferred.

The tests carried out to identify the precursors of B or B$_1$ are in detail the following:

Test 4 is a colorimetric test which affords to establish whether the precursors of B or B$_1$ inhibit the production of radicals from DPPH (2,2-diphenyl-1-picryl-hydrazyl) (M. S. Nenseter et Al., Atheroscler. Thromb. 15, 1338–1344, 1995). 100 μM solutions in methanol of the tested substances are prepared, and an aliquot of each of said solutions is added to a DPPH solution in methanol 0.1 M. After having stored the solutions at room temperature away from light for 30 minutes, their absorbances are read at the wave length of 517 nm, together with that of the corresponding DPPH solution at the same concentration. The absorbance decrease with respect to that of the solution of DPPH at the same concentration of the test solutions is determined. The effectiveness of the tested compound in inhibiting formation of radicals by DPPH is expressed by the following formula:

(1−A$_S$/A$_C$)33 100 wherein A$_S$ and A$_C$ are respectively the absorbance values of the solution containing the test compound together with DPPH and of the solution containing only DPPH; the compounds precursor of B or B$_1$ meet test 4 when the inhibition percentage of radical production from DPPH, expressed as a percentage according to the above equation, is higher than or equal to 50% at the indicated concentration ($10^{-4}$ M).

If the precursors of B or B$_1$ do not meet test 4, test 5 is carried out.

Test 5 is a colorimetric test wherein 0.1 ml aliquots of $10^{-4}$ M methanolic solutions of the tested products are added to test tubes containing a solution formed by 0.2 ml of 2 mM desoxyribose, 0.4 ml of phosphate buffer pH 7.4 100 mM and 0.1 ml of 1 mM $Fe^{II}(NH_4)_2(SO_4)_2$ in 2 mM HCl. The test tubes are then maintained at 37° C. for one hour. Then in each test tube 0.5 ml of a 2.8% solution in trichloroacetic acid water and 0.5 ml of an aqueous 0.1 M solution of thiobarbituric acid are added, in the order. A reference blank is formed by adding to a test tube containing only the above described aqueous solution of reactants 0.1 ml of methanol. The test tubes are closed and heated in an oil bath at 100° C. for 15 minutes. A pink coloration is developed the intensity of which is proportional to the quantity of desoxyribose undergone to radical oxidative degradation. The solutions are cooled at room temperature and their absorbances are read at 532 nm against the blank. The inhibition induced by the precursor of B or B$_1$ or C=—T$_C$—Y—H in comparison with the radical production by $Fe^{II}$ is determined by means of the following formula:

(1—A$_S$/A$_C$)×100 wherein A$_S$ and A$_C$ are respectively the absorbance values of the solution containing the tested compound+the iron salt and that of the solution containing only the iron salt, the compound meets test 5 when the inhibition percentage of radical production as above defined from the precursor of B or B$_1$ or C=—T$_C$—Y—H is higher than or equal to 50%.

Y$^3$ in formula (III) is preferably selected from the following:

(Y1)

(Y2)

(Y3)

(Y4)

(Y5)

(Y6)

(Y7)

(Y8)

(Y9)

(Y10)

(Y11)

(Y12)

(Y13)

(Y14)

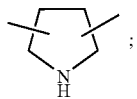
(Y15)

The most preferred of $Y^3$ is Y12 (pyridyl) substituted in positions 2 and 6. The bonds can find also in asymmetric position, for example Y12 (pyridyl) can be substituted also in position 2 and 3; Y1 (pyrazol) may be 3,5-disubstituted.

The compounds according to the present invention of formula (I) and (II) can be transformed into the corresponding salts. For example one way to form salts is the following: when in the molecule one nitrogen atom sufficiently basic to be salified, in organic solvent such as for example acetonitrile, tetrahydrofuran, is present, it is reacted with an equimolecular amount of the corresponding organic or inorganic acid.

Preferably in the formula of the invention compounds Y or Y' of formula (III) is present.

Examples of organic acids are: oxalic, tartaric, maleic, succinic, citric acids.

Examples of inorganic acids are: nitric, hydrochloric, sulphoric, phosphoric acids.

In the steroid precursors preferably R"=—CO—CH$_2$OH, —CH(CH$_3$)—CH$_2$—CH$_2$—COOH.

Among the steroid precursors those having the hydroxyl function in position 3 or in position 11, or having in R" an hydroxyl or carboxylic function in terminal position, are preferred.

The steroid precursors of A which can be mentioned and which are preferred, are those listed hereinunder, obtainable according to the processes known in the art.

As precursors and respective processes, those for example described in The Merck Index, ed. 12 of 1996, herein incorporated by reference, can be mentioned. The precursors (according to the Merck nomenclature) are the following, wherein $H_2$, H, R, R', R" have the meaning mentioned in the compounds listed herein: Budesonide, Hydrocortisone, Alclomethasone, Algestone, Beclomethasone, Betamethasone, Chloroprednisone, Clobetasol, Clobetasone, Clocortolone, Cloprednol, Cortisone, Corticosterone, Deflazacort, Desonide, Desoximethasone, Dexamethasone, Diflorasone Diflucortolone, Difluprednate, Fluazacort, Flucloronide, Flumethasone, Flunisolide, Fluocinolone Acetonide, Fluocinonide, Fluocortyn Butyl, Fluocortolone, Fluorometholone, Fluperolone Acetate, Fluprednidene Acetate, Fluprednisolone, Flurandrenolide, Formocortal, Halcinonide, Halobetasol Propionate, Halomethasone, Halopredone Acetate, Hydrocortamate, Loteprednol Etabonate, Medrysone, Meprednisone, Methylprednisolone, Mometasone Furoate, Paramethasone, Prednicarbate, Prednisolone, Prednisolone 25-Diethylaminoacetate, Prednisolone Sodium Phosphate, Prednisone, Prednival, Prednylidene, Rimexolone, Triamcinolone, Triamcinolone Acetonide, 21-Acetoxypregnenolone, Cortivazol, Amcinonide, Fluticasone Propionate, Mazipredone, Tixocortol, Triamcinolone Hexacetonide, Ursodesoxycholic acid, Chenodeoxycholic acid, Mitatrienediol, Moxestrol, Ethynylestradiol, Estradiol, Mestranol.

Unexpectedly the invention products of the formulas (I) and (II), in conditions of oxidative stress, have an improved therapeutic index compared with the precursor steroids. For illustrative purposes the above mentioned tests are referred to the following compounds (see the tables attached to the description):

Test 4 (test for the precursor of B and $B_1$, ref. Table III)
N-acetylcysteine inhibits of 100% radical production from DPPH, therefore it meets test 4 and it can be used as precursor of B or $B_1$.
4-thiazolidincarboxylic acid does not inhibit radical production from DPPH, therefore it does not meet test 4: it can be used as precursor of B or $B_1$ if it meets test 5.

Test 5 (test for the precursor of B and $B_1$ or of C—T$_C$—Y—H, ref. Table IV)
4-thiazolidincarboxylic acid meets test 5 since the inhibition is of 100%. Therefore the compound can be used as precursor of B or $B_1$ in formula (I).

The compounds of the invention can be used in the same therapeutic indications of the precursor drug with the above mentioned advantages.

The compounds of formula (I) or (II) are prepared by synthesis methods mentioned hereinunder.

The choice of the reactions for each method depends on the reactive group present in the steroid molecule, in the precursor compound of B or $B_1$, which can be, as above mentioned, bivalent or monovalent, and in the precursor compound of C.

The reactions are carried out with well known methods in the prior art, which allow to obtain bonds among the steroid, the precursor compound of B or $B_1$ and the precursor compound of C as above defined.

When the reactive function of the steroid (for example —COOH, —OH) is involved in a covalent bond, for example of ester, amide, ether type, said function can be restored with the well known methods in the prior art.

Some synthesis schemes for obtaining the compounds of the invention are reported hereinafter:

A) Synthesis of the Compounds of Formula (I).
1. Synthesis of the compound obtained by reaction between the steroid and the compound precursor of B.
1a. When the steroid contains a carboxylic function (general formula: R—COOH) and the functional group of the precursor compound of B which binds itself to the carboxylic function has the formula XZ, X being as above defined and Z=H, the effected reactions depend on the nature of the second reactive group present in the precursor compound of B.
1a.1 When the second reactive group present in the precursor compound of B is a carboxylic group, the synthesis general scheme expects the initial formation of the acyl halide of the R—COHal steroid (Hal=Cl, Br) and the subsequent reaction with the HX group of the precursor compound of B:

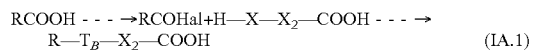

(IA.1)

$X_2$, $T_B$ being as above defined.

When in the two reaction compounds other functional groups COOH and/or HX are present, they must be protected before the reaction according to the methods known in the prior art; for example as described in the publication by Th. w. Greene: "protective groups in organic synthesis", Harward University Press, 1980.

The RCOHal acylhalide is prepared according to the known methods in the prior art, for example by thionyl or oxalyl chloride, $P^{III}$ or $P^V$ halides in inert solvents under the reaction conditions, such as for example toluene, chloroform, DMF, etc.

Specifically, when the HX group of the precursor compound of B is $NH_2$, or OH or SH, the steroid of formula R—COOH is first converted into the corresponding acyl halide RCOHal, as above mentioned, and then reacted with the HX group of the precursor compound of B in the presence of an organic base, such as triethylamine, pyridine, etc. using an inert solvent in the reaction conditions such as toluene, tetrahydrofuran, etc. at a temperature in the range 0° C.–25° C.

Alternatively to the previous synthesis, the steroid of formula R—COOH can be treated with an agent activating the carboxyl group selected from N,N'-carbonyldiimidazol (CDI), N-hydroxybenzotriazol and dicyclohexylcarbodiimide in solvent such as for example DMF, THF, chloroform etc. at a temperature in the range −5° C.–50° C. and the obtained commpound reacted in situ with the reactive function of the precursor compound of B for obtaining the compound of formula (IA.1).

1a.2 When the precursor compound of B contains two functional groups XZ, equal to or different from each other, X being as above defined and Z=H, the steroid having formula R—COOH is first treated with an agent activating the carboxyl group, as above described in 1a.1, and then with the precursor compound of B, after having protected one of the two reactive HX groups, for example with acetyl or tert-butyloxycarbonyl, restoring the initial function at the synthesis end. The scheme is the following:

$$RCOOH \xrightarrow{CDI, \ HX-X_2-X-G} R-T_B-X_2-X-G \cdots \rightarrow \cdots \rightarrow R-T_B-X_2-XH$$
(IA. 2)

wherein X, $T_B$, $X_2$ are as above defined and G is a protective group of the HX function.

2. Nitroxyderivative Synthesis.

2a.1 When the compound obtained at the end of the previous step 1a. has formula (IA.1), the acid can be converted into the corresponding sodic salt and one can then follow the known prior art methods for preparing the final compound, for example according to one of the following synthesis schemes:

A.)

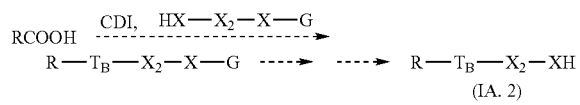
(1A.1b)
$$R-T_B-X_2-T_{BI}-T_C-Y-NO_2$$

wherein $T_B$, $X_2$, $T_{BI}$, $T_C$ are as above defined, $R_4$ is selected from Cl, Br, Y is as above defined, $X_1$ is the Y radical free from the oxygen atom, $R_3$ is Cl, Br, iodine, OH. If $R_3$=OH the compound of formula (1A.1b) is subjected to halogenation, for example with $PBr_3$, $PCl_5$, $SOCl_2$, $PPh_3+I_2$, and then reacted with $AgNO_3$ in organic solvent such as acetonitrile, tetrahydrofuran. If $R_3$ is Cl, Br, Iodine, the compound of formula (1A.1b) is directly reacted with $AgNO_3$ as above mentioned.

B.)

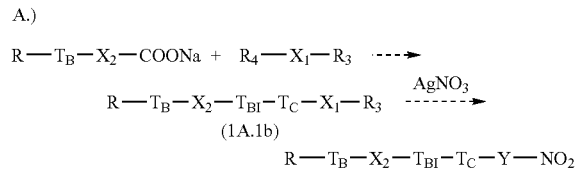

C.)

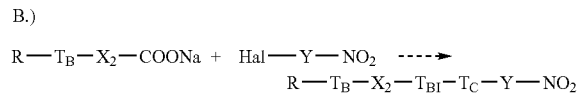
(1A.1C)

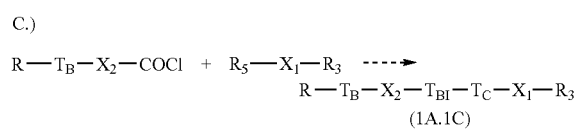

wherein $R_5$=OH or $NHR_{1C}$, $R_{1C}$, $R_3$ and the other symbols being as above defined.

When $X_1$ is a linear $C_4$ alkyl, the corresponding acid $R-T_B-X_2$—COOH is reacted with triphenylphosphine in the presence of an halogenating agent such as $CBr_4$ or N-bromosuccinimide in tetrahydrofuran obtaining the compound (1A.1c) wherein $R_3$=Br.

2a.2 When the compound obtained at the end of the previous step 1a. has formula (IA.2), the corresponding nitroxyderivative is obtained by treating an halogen-carboxylic acid of formula Hal—$X_1$—COOH, $X_1$ being as above defined, first with an agent activating the carboxyl group as described in 1A.1, and then with the compound of formula (IA.2), obtaining an halogen derivative, which is isolated and then dissolved in organic solvent, (ref. paragraph 2a.1), and treated with silver nitrate. The global reaction scheme is the following:

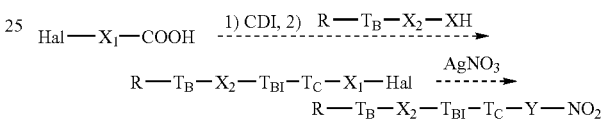

wherein $T_B$, $X_2$, $T_{BI}$, $T_C$, Y are as above defined.

Alternatively, the halide Hal—$X_1$—COCl can be used, wherein Hal is preferably bromine, which is let react with the compound of formula (IA.2).

1b. When the reactive function of the steroid is —OH (general formula: R—OH), the two functional groups present on the precursor compound of B can be the following:

1b.1 A carboxylic group, which reacts with the steroid OH function, and a HX group, the latter reactive group of the precursor compound of B being equal to or different from the steroid functional group. The formula of the precursor compound of B is of the H—X—$X_2$—COOH type, wherein X and $X_2$ are as above defined.

The H—X— function of the precursor compound of B is protected according to the known prior art methods and the carboxyl is reacted, as above mentioned, according to the following scheme:

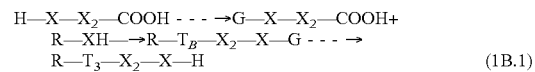
(1B.1)

At the end of the reaction the HX function of the precursor compound of B is restored.

1b.2 When the precursor compound of B contains two carboxylic groups, it is treated with an equimolar amount of an agent activating the carboxyl group under the conditions previously described in 1a.1, and then reacted with the reactive OH function of the steroid molecule. Possible other reactive functions of HX type present in the two compounds must be carefully protected as previously mentioned. Lastly a compound of formula R—$T_B$—$X_2$—COOH (1B.2) is obtained.

2b. Nitroxyderivative Synthesis.

2b.1 To obtain the final nitroxyderivative starting from the compound of formula R—$T_B$—$X_2$—X—H (1B.1), obtained at the end of the synthesis described in 1b.1, the (1B.1) compound is reacted with an halogenacid of formula Hal—$X_1$—COOH which has been treated as previously described in paragraph 1a.1, or with the corresponding halogenacid chloride, the resulting compound is dissolved in organic solvent, for example acetonitrile or tetrahydrofuran and reacted with silver nitrate.

2b.2 To obtain the final nitroxyderivative starting from the compound of formula $R-T_B-X_2-COOH$ (1B.2), obtained at the end of the syntheses described in 1b.2, the acid is transformed into the corresponding sodic salt, it is reacted with a $R_4-X_1-R_3$ compound, previously defined in the reaction A. scheme of paragraph 2a.1, obtaining according to the same process therein mentioned the final nitroxyderivative. Alternatively, when $X_1$ is a linear $C_4$ alkyl, the acid (1B.2) is reacted with triphenyl-phosphine in the presence of an halogenating agent such as $CBr_4$ or N-bromosuccinimide in tetrahydrofuran and the resulting compound dissolved in organic solvent for example acetonitrile, tetrahydrofuran, is reacted with silver nitrate.

2b.3 Alternatively to the synthesis process according to 1b.1 and 2b.1, it is possible to react in a first step the HX— function of the precursor compound of B $HX-X_2-COOH$ with the acyl chloride of an halogenacid of formula $Hal-X_1-CO-Cl$, wherein Hal is preferably Br, and subsequently the carboxylic function of the so obtained compound, with the steroid of formula R—OH. In the third and last step the —Hal group is substituted with —$ONO_2$ according to the process described in 2b.1. The reaction scheme is the following:

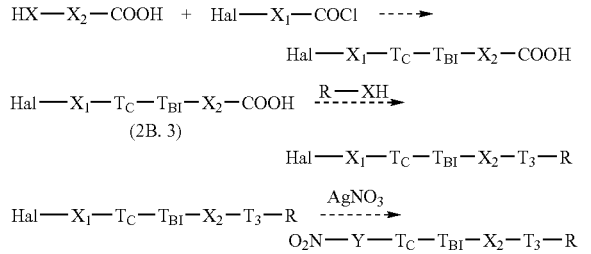

wherein $T_C$, $T_{BI}$, $T_B$, $X_2$, $X_1$, Y are as above defined.

In the previous scheme the nitration can alternatively be carried out on the acid compound of formula (2B.3).

In the above mentioned processes the steroid reaction with the precursor of B for the compounds of formula (I) is not carried out when $b_0=0$, and in the reaction with the precursor compound of C the steroid with its reactive function is directly used.

B) Synthesis of Compounds of Formula (II).

1a. When the steroid reactive function is a carboxylic group and the precursor compound of $B_1$ contains only one functional reactive group of formula XH, X being as above defined, the steroid is initially converted into the corresponding acyl-halide (RCOCl), or treated with an agent activating the carboxyl group as described in 1a.1, and then reacted with the HX function of an halogen-acid compound, said function being equal to or different from that present on the precursor compound of $B_1$, said halogen-acid having the formula:

wherein $X_1'$ is Y' as above defined without the oxygen atom through which the —$NO_2$ group is linked, X and Hal are as above defined.

The compound (IIA.1) can be obtained with the known method of the prior art.

For example when X=NH, it can be obtained from the corresponding hydroxy-aminoacid, by protecting the aminic group by the corresponding tert-butyl-oxycarbonyl derivative and transforming the hydroxyl function into halogen group as described for the compound halogenation (1A.1b) in 2a.1.

The free carboxylic function of the compound resulting from the reaction with the steroid molecule is reacted with the function present in the molecule of the precursor of $B_1$, as previously illustrated in 1a.1 for the reaction between the steroid of formula R—COOH and the precursor compound of B. In the final step the halogen atom (Hal) present on the radical $X_1$ is substituted with an $ONO_2$ group by adding $AgNO_3$ to an organic solution of the compound. The reaction scheme is the following, exemplified starting from the RCOCl halide:

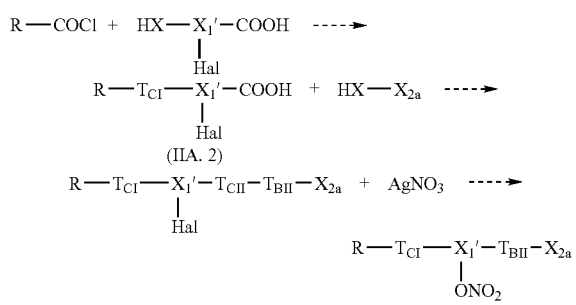

1b. When the steroid reactive function is a OH group and the precursor compound of $B_1$ contains a reactive group of general formula XH, HX wherein X is as above defined, being equal to or different from OH, the synthesis is carried out starting from an halogendiacid compound of formula

$X_1'$ being as above defined, said compound being prepared from the corresponding hydroxy-diacid as described for the halogenation of the compound (1A.1b) in 2a.1. The halogendiacid compound is treated with an equimolar amount of an agent activating the carboxyl group, under the conditions previously described in 1a.1., and then it is reacted with the reactive function of the steroid molecule. In the subsequent step the second carboxylic function is treated with an activating agent, as previously made for the first, and reacted with the precursor compound of $B_1$ according to the following scheme:

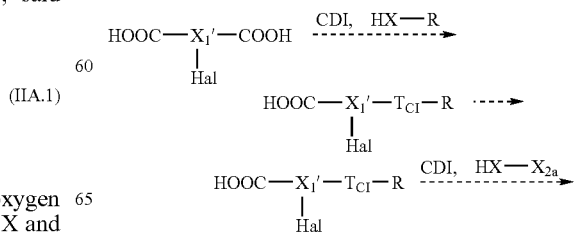

-continued

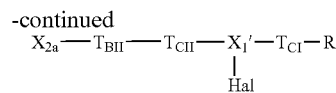

The halogen atom is then substituted with the ONO$_2$ group as above mentioned.

3. Synthesis of the Nitroso (s=1) Derivatives of Formula (I).

3a.1 The compound of formula (1A.1b) wherein R$_3$=OH is reacted with sodium nitrite in a solvent formed of a mixture of water with tetrahydrofuran in the presence of hydrochloric acid. The reaction is widely illustrated in the prior art.

The general scheme is the following:

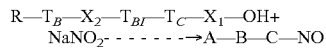

3a.2 If the compound obtained at the end of step A has formula (IA.2) the corresponding nitroso derivative is obtained by treating an hydroxyacid of formula HO—X$_1$—COOH, X$_1$ being as above defined, first with an agent activating the carboxyl group, as described in 1a.1, then with 1A.2 and the resulting product with sodium nitrite as described in 3a.1.

3b.1 To obtain the nitroso derivative starting from the compound of formula R—T$_B$—X$_2$—XH (1B.1) obtained at the end of the synthesis described in 1b.1, the compound (1B.1) is reacted with an hydroxyacid as described in 3a.2.

3b.2 To obtain the nitroso derivative from the compound of formula R—T$_B$—X$_2$—COOH (1B.2) obtained at the end of the synthesis described in 1b.2, the acid is transformed into the sodic salt and reacted with a compound Hal—X$_1$—OH, as previously described, and the obtained alcohol is treated as described in 3a.1.

4) Synthesis of the Nitroso Derivatives of Formula (II)

4a.1 When the steroid reactive function is a carboxylic group (general formula R—COOH) and the precursor compound of B$_1$ contains only one functional reactive group of Formula XH, X being as above defined, R—COOH is initially converted into the corresponding acyl-halide or treated with an agent activating the carboxyl group as described in 1a.1, and then reacted with the HX function of an hydroxy-acid compound, said function being equal to or different from that present on the precursor compound of B$_1$, said hydroxy-acid having the formula:

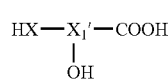

(4A. 1)

wherein X$_1$' is Y' as above defined without the oxygen atom through which the —NO group is linked, X is as above defined.

The free carboxylic function of the compound resulting from the reaction with the steroid molecule is reacted with the function present in the molecule of the precursor compound of B$_1$, as previously illustrated in 1a.1 for the reaction between the R—COOH acid and the precursor compound of B. In the final step the alcohol is transformed into the nitroso-derivative as described in 3a.1.

The reaction scheme is the following, exemplified starting from the RCOCl acid halide:

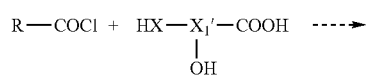

-continued

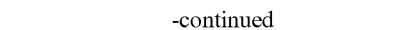

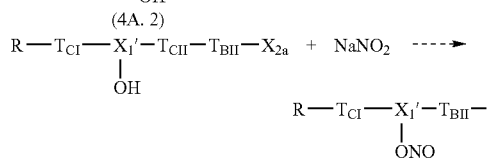

4b. When the reactive steroid function is a OH group and the precursor compound of B$_1$ contains a reactive group of general formula XH, HX in which X is as above defined being equal to or different from OH, the synthesis is carried out starting from an hydroxydiacid compound of formula

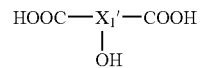

X$_1$' being as above defined, said hydroxydiacid compound is treated with an equimolar amount of an agent activating the carboxyl group, under the conditions previously described in 1a.1., and then it is reacted with the steroid reactive function. In the subsequent step the second carboxylic function is treated with an activating agent, as previously made for the first one, and reacted with the precursor compound of B$_1$ according to the following scheme:

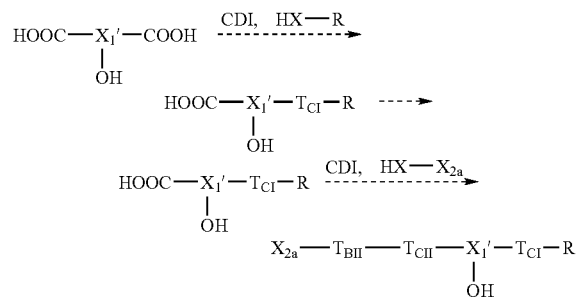

The obtained compound is reacted as described in 3a.1.

The compounds object of the present invention are formulated in the corresponding pharmaceutical compositions for parenteral, oral and topic use according to the well known methods in the art, together with the usual excipients; see for example the volume "Remington's Pharmaceutical Sciences 15a Ed."

The amount on molar basis of the active principle in these formulations is the same, or lower, in comparison with that used of the corresponding precursor drug.

The daily administrable doses are those of precursor drugs, or in the case lower. The daily doses can be found in the publications of the field, such as for example in "Physician's Desk reference".

The following examples have the purpose to illustrate the invention and are not to be considered as limitative of the same.

EXAMPLE 1

Preparation of 3-[4-[(3α,5β,7β)-3,7-dihydroxy-colan-24-oiloxy]-3-methoxyphenyl]-2-propenoic acid 4-nitroxybutyl ester

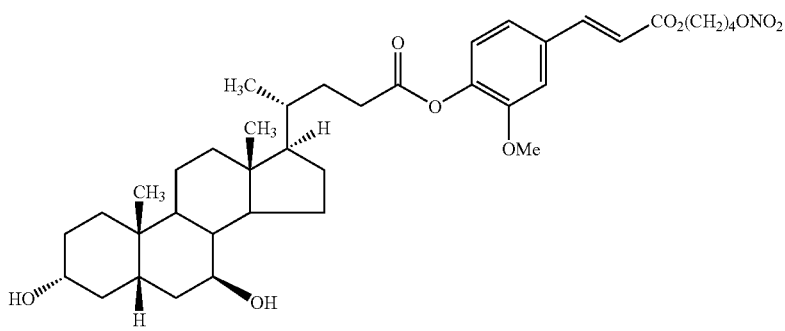

wherein the precursor steroid is ursodesoxycholic acid of formula (XL), the precursor of B is ferulic acid of formula (DII):

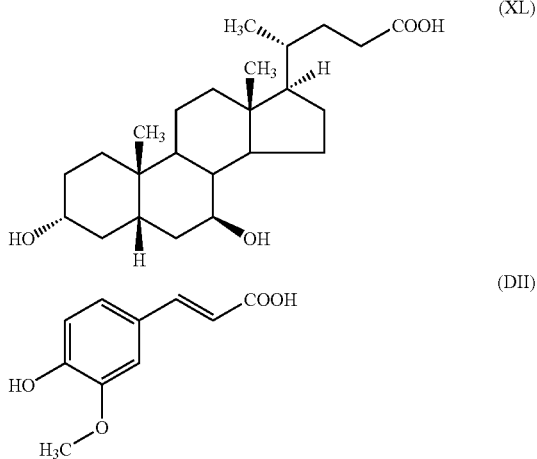

a) Synthesis of the 3-(4-hydroxy-3-methoxyphenyl)-2-propenoic acid 4-bromobutyl ester To a solution of 3-(4-hydroxy-3-methoxyphenyl)-2-propenoic acid (10 g, 51.5 mmoles) in THF (400 ml) triphenylphosphine (2.7 g, 10.3 mmoles) and carbon tetrabromide (34.16 g, 10.3 mmoles) are added and the solution is left at room temperature, under magnetic stirring, for 48 hours. The solid is filtered and then evaporated at reduced pressure. The obtained crude product is purified by chromatogrphy on silica gel eluting with n-hexane/ethyl acetate 7/3. 9 g of 3-(4-hydroxy-3-methoxyphenyl)-2-propenoic acid 4-bromobutyl ester are obtained. M.p.=86–89° C.

b) Synthesis of the 3-[4-[(3α,5β,7β)-3,7-dihydroxy-colan-24-oiloxy]-3-methoxyphenyl]-2-propenoic acid 4-bromobutyl ester To a solution of (3α,5β,7β)-3,7-dehydroxycolan-24-oic acid (2.9 g, 7.38 mmoles) dissolved in chloroform (25 ml) and dimethylacetamide (25 ml), 3-(4-hydroxy-3-methoxyphenyl)-2-propenoic acid 4-bromobutyl ester (2.73 g, 8.28 mmoles) is added under stirring. To the solution cooled at 0° C., kept under stirring, N,N'-dicyclohexylcarbodiimide (2 g, 9.7 mmoles) and 4-dimethylamino pyridine (100 mg, 0.81 mmoles) are added. After 1 hour the mixture is heated to room temperature, after 24 hours the precipitate is filtered, the solvent is evaporated at reduced pressure. The residue is treated with ethyl acetate (150 ml) and washed with water (3×100 ml). After the organic phase is anhydrified with sodium sulphate the solvent is evaporated. The obtained crude product is purified by chromatography on silica gel column eluting with n-hexane/ethyl acetate 1/9. 2.5 g of 3-[4-[(3α,5β,7β)-3,7-dihydroxycolan-24-oiloxy]-3-methoxyphenyl-2-propenoic acid 4-bromobutyl ester are obtained.

c) Synthesis of the 3-[4-[(3α,5β,7β)-3,7-dihydroxy-colan-24-oiloxy]-3-methoxyphenyl]-2-propenoic acid 4-nitroxybutyl ester To a solution of 3-[4-[(3α,5β,7β)-3,7-dehydroxycolan-24-oiloxy]-3-methoxyphenyl]-2-propenoic acid 4-bromobutyl ester (2.3 g, 3.27 mmoles) in acetonitrile (20 ml) and tetrahydrofuran (5 ml) silver nitrate (0.84 g, 4.94 mmoles) is added under stirring and the mixture is heated to 80° C. under magnetic stirring for 6 hours. When the reaction is over the precipitate is filtered and the solvent is evaporated. The obtained crude product is purified by chromatography on silica gel column eluting with methylene chloride/ethyl acetate 3/7. 1.5 g of 3-(4-[(3α,5β, 7α)-3,7-dehydroxycolan-24-oiloxy]-3-methoxyphenyl]-2-propenoic acid 4-nitroxybutyl ester are obtained. Total yield 32%.

| Elementary analysis | | | |
|---|---|---|---|
| Calculated | C 66.55% | H 8.08% | N 2.04% |
| Found | C 66.59% | H 8.14% | N 1.99% |

EXAMPLE 2

Preparation of 3-[4-[(3α,5β,7α)-3,7-dihydroxy-colan-24-oiloxy]-3-methoxyphenyl]-2-propenoic acid 4-nitroxybutyl ester

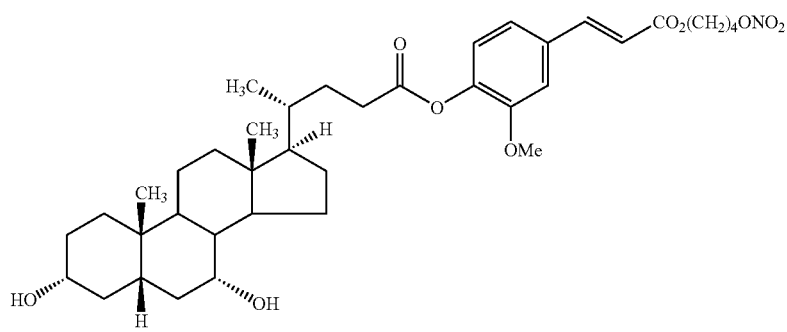

wherein the precursor steroid is chenodeoxycholic acid of formula (XLI) and the B precursor is ferulic acid of formula (DII)

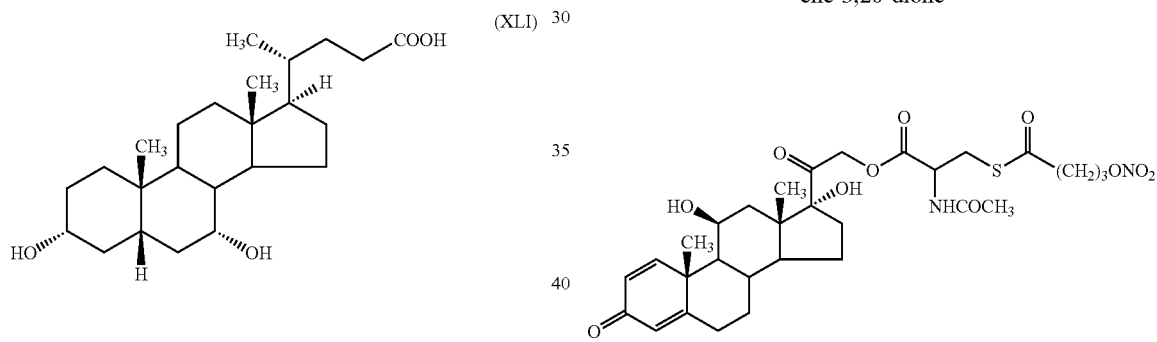

The compound is prepared following the procedure reported in Example 1. Total yield 28%.

| Elementary analysis | | | |
|---|---|---|---|
| Calculated | C 66.55% | H 8.08% | N 2.04% |
| Found | C 66.64% | H 8.13% | N 1.94% |

EXAMPLE 3

Preparation of (11β)-11,17-dihydroxy-21[N-acetyl-S-(4-ni-troxybutyroyl)cysteinyloxy]-pregn-1,4-diene-3,20-dione

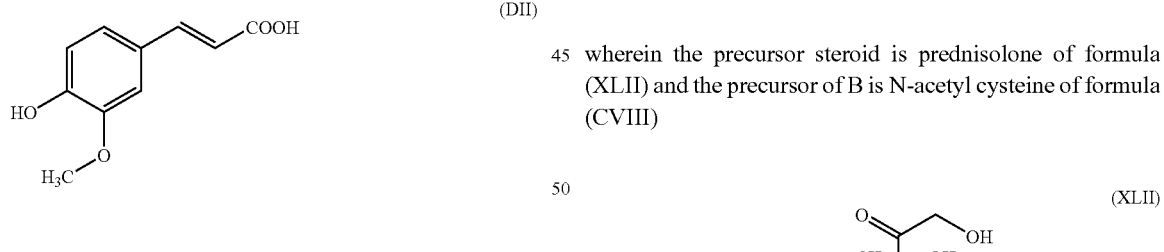

wherein the precursor steroid is prednisolone of formula (XLII) and the precursor of B is N-acetyl cysteine of formula (CVIII)

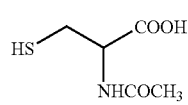

a) Synthesis of N-acetyl-S-(4-bromobutyroyl)cysteine

A solution of 4-bromobutyric acid (5.1 g, 30.6 mmoles) and 1,1'-carbonyldiimidazol (5.61 g, 34.6 mmoles)) in chloroform (50 ml) is left at room temperature under stirring for 1 hour. To the reaction mixture N-acetyl cysteine (5 g, 30.6 mmoles) dissolved in N,N-dimethylformamide (5 ml) and sodium ethylate (50 mg) is added under stirring. After 24 hours the solution is washed with HCl 1% and brine, the organic phase is anhydrified with sodium sulphate and evaporated at reduced pressure. The obtained crude product is purified by chromatography on silica gel column, eluting with ethyl acetate/chloroform 7/3. N-acetyl-S-(4-bromobutyroyl) cysteine is obtained.

b) Synthesis of (11β)-11,17-Dihydroxy-21[N-acetyl-S-(4-bromobutyroyl)cysteinyloxy]-pregn-1,4-diene-3,20-dione To a solution of N-acetyl-S-(4-bromobutyroyl)cysteine (2.7 g, 8.64 mmoles) and (11β)-11,17,21-trihydroxypregn-1,4-diene-3,20-dione (3.2 g, 8.86 mmoles) in tetrahydrofuran (100 ml) cooled at 0° C. and kept under stirring, N,N'-dicyclohexylcarbodiimide (1.9 g, 9.2 mmoles) and 4-dimethylaminopyridine (100 mg, 0.8=moles) are added. After 1 hour the mixture is heated to room temperature, after 24 hours the precipitate is filtered, the solvent is evaporated at reduced pressure. The residue is treated with ethyl acetate (150 ml) and washed with water (3×00 ml). After having anhydrified the organic phase with sodium sulphate the solvent is evaporated. The obtained crude product is purified by chromatography on silica gel column eluting with chloroform/ethyl acetate 3/7. 0.94 g of (11β)-11,17-dehydroxy-21[N-acetyl-S-(4-bromobutyroyl)cysteinyloxy]-pregn-1,4-diene-3,20-dione are obtained.

c) Synthesis of (11β)-11,17-Dihydroxy-21[N-acetyl-S-(4-nitroxybutyroyl)cysteinyloxy]-pregn-1,4-diene-3,20-dione To a solution of (11β)-11,17-dehydroxy-21[N-acetyl-S-(4-bromobutyroyl)cysteinyloxy]-pregn-1,4-diene-3,20-dione (0.8 g, 1.28 mmoles) in acetonitrile (10 ml) and tetrahydrofuran (5 ml) silver nitrate (0.4 g, 2.35 mmoli) is added under stirring and the mixture is heated to 80° C. under magnetic stirring for 20 hours. At the end of the reaction the precipitate is filtered and the solvent is evaporated. The obtained crude product is purified by chromatography on silica gel column eluting with methylene chloride/ethylacetate 3/7. (11β)-11,17-dehydroxy-21[N-acetyl-S-(4-nitroxybutyroyl)cysteinyloxy]-pregn-1,4-diene-3,20-dione is obtained. Total yield 12%.

| Elementary analysis | | | | |
|---|---|---|---|---|
| Calculated | C 56.59% | H 6.33% | N 4.40% | S 5.04% |
| Found | C 56.63% | H 6.38% | N 4.36% | S 5.01% |

EXAMPLE 4

Preparation of (11β)-11,17-Dihydroxy-21[N-acetyl-S-(4-nitroxybutyroyl)cysteinyloxy]-pregn-4-ene-3,20-dione

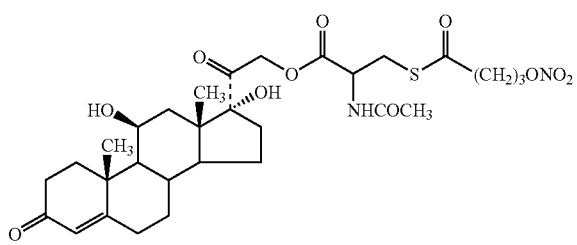

wherein the precursor steroid is hydrocortisone of formula (XLIII) and the precursor of B is N-acetyl cysteine of formula (CVIII)

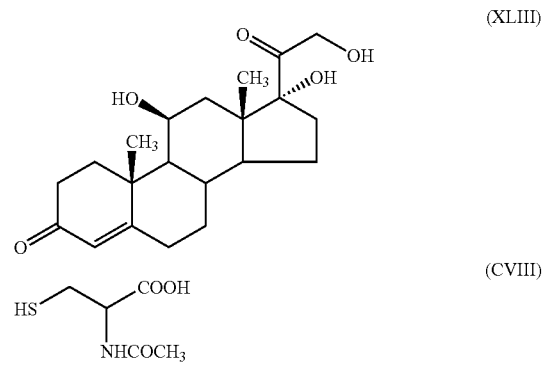

The compound is prepared according to the procedure reported in Example 3. Total yield 15%.

| Elementary analysis | | | | |
|---|---|---|---|---|
| Calculated | C 56.37% | H 6.78% | N 4.39% | S 5.02% |
| Found | C 56.39% | H 6.81% | N 4.31% | S 4.93% |

EXAMPLE 5

Preparation of (11β,16α)-9-Fluoro-11,17-dihydroxy-21[N-acetyl-S-(4-nitroxybutyroyl)cysteinyloxy]-16-methylpregn-1,4-diene-3,20-dione

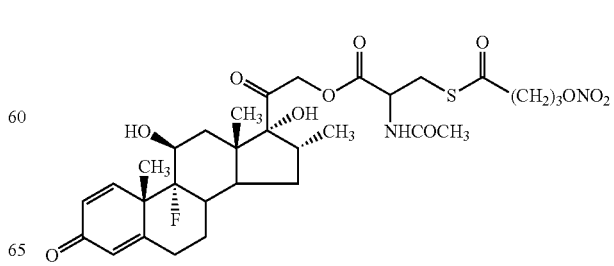

wherein the precursor steroid is desamethasone of formula (X-LIV) and the precursor of B is N-acetyl cysteine of formula (CVIII)

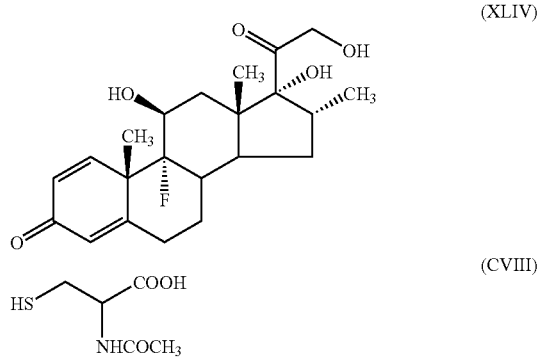

The compound is prepared according to the procedure reported in Example 3. Total yield 17%.

Elementary analysis

| | | | | |
|---|---|---|---|---|
| Calculated | C 55.68% | H 6.18% | N 4.19% | S 4.79% |
| Found | C 55.72% | H 6.22% | N 4.15% | S 4.75% |

Pharmacological Tests

EXAMPLE

Acute Toxicity

Acute toxicity has been evaluated by administering to a group of 10 rats weighing 20 g a single dose of each of the tested compounds, by cannula, by os in an aqueous suspension of carboxymethylcellulose 2% w/v.

The animals are kept under observation for 14 days. In no animal of the group toxic symptoms appeared even after a 100 mg/Kg dose administration.

Example F1

Experimental in vivo model with $N^w$nitro-L-arginine-methyl ester (L-NAME): effect of the precursor steroids and of the corresponding compounds according to pre resent invention on the endothelial dysfunction induced by L-NAME.

The experimental model adopted s according to J. Clin. Investigation 90, 278–281,1992.

The endothelial dysfunction is evaluated by determining the damage the hepatic damage (GPT increase), and the vascular endothelium or cardiovascular damage (blood hypertension) induced by L-NAME administration.

The animals (Long Evans rats, average weight 350–450 g) are divided in groups as herein below described. The group receiving L-NAME is treated for 4 weeks with said compound dissolved at the concentration of 400 mg/liter in drinking water. The following groups (No. 10 animals for group) are constituted:

A) Control Groups:
1° group: treatment: only carrier (physiologic solution),
2° group: treatment: carrier+L-NAME.

B) Groups Treated with the Drug:
3° group: treatment: carrier+drug,
4° group: treatment: carrier+drug+L-NAME.

The drugs screened in the test are hydrocortisone, desamethasone, prednisolone, chenodeoxycholic acid, ursodesoxycholic acid and the corresponding derivatives according to the present invention.

In those groups of rats treated, respectively, with hydrocortisone, desamethasone, prednisolone and thereof corresponding compounds according to the present invention, the blood-pressure is determined.

In those groups of rats treated, respectively, with ursodesoxycholic acid and chenodeoxycholic acid and thereof corresponding compounds according to the present invention, GPT is determined.

Each drug is administered by intraperitoneal route once a day for 4 weeks.

At the end of the four weeks access to water is prevented and after 24 hours the animals are sacrificed.

Four hours, after the last administration the blood-pressure is determined.

Damage to the vascular endothelium is determined, as said by the cardiovascular effects induced by L-NAME (increase of the blood pressure). The hepatic damage is determined by evaluation of the glutamic-pyruvic transaminase (GPT increase) after sacrifice.

Results are reported in Tables I and II. The % blood-pressure and GPT values are referred to the corresponding value found in the animals of the 1st control group. The average value of the blood pressure in this group was of 105 mmHg.

The results obtained show that the steroidal precursors cause hepatic damage (ursodesoxycholic acid and chenodeoxycholic acid) and arterial hypertension (hydrocortisone, desamethasone, prednisolone). GPT and blood pressure values of the treated rats are higher compared both with the corresponding groups treated with drug in the absence of L-NAME and with the controls treated with L-NAME. The products of the invention are instead better tolerated in comparison with the corresponding precursors, even in animals not pretreated with L-NAME.

Example F2

Test 4: Inhibition of the Radical Production from DPPH of Some Substances Used to Prepare the Precursors of B or B1

The method is based on a colorimetric test in which DPPH (2,2-diphenyl-1-picryl-hydrazyl) is used as the compound-forming radicals (M.S. Nenseter et Al., Atheroscler. Thromb. 15, 1338–1344, 1995).

Solutions in methanol of the tested substances at a final concentration 100 μM are initially prepared. 0.1 ml of each of these solutions are added to aliquots of 1 ml of a methanol solution C.1 M of DPPH and then the final volume is brought to 1.5 ml. After having stored the solutions at room temperature away from light for 30 minutes, the absorbance at the wave length of 517 mm is read. It is determined the absorbance decrease with respect to the absorbance of a solution containing the same concentration of DPPH.

The efficacy of the test compound to inhibit the production of radicals, otherwise said antiradical activity, is expressed by the following formula:

$$(1-A_S/A_C) \times 100$$

wherein $A_S$ and $A_C$ are, respectively, the absorbance values of the solution containing the test compound together+ DPPH and of the solution containing only DPPH.

The compound to be used as precursor of B or $B_1$ according to the present invention meets test 4 if it inhibits radical production from DPPH in a percent equal to or higher than 50%.

In Table III are reported the results obtained in said test with the following compounds: N-acetylcysteine, cysteine, ferulic acid, (L)-carnosine, gentisic acid, 4-thiazolidin carboxylic acid Ard 2-oxc-4-thiazolidincarboxylic acid.

Table III shows she following:

N-acetylcysteine, cysteine, ferulic acid, (L)-carnosine, gentisic acid meet test 4 since they inhibit the production of radicals induced by DPPH to an extent higher than 50%. Therefore they can be use as precursors of the B compound in the synthesis of the compounds according to the present invention.

4-thiazolidin carboxylic acid and the 2-oxo-4-thiazolidin carboxylic acid do not meet test 4 since they do not inhibit radical production from DPPH. Therefore they can be used as precursors of B or $B_1$ if they meet test 5.

Example F3

Test 5: Inhibition of the radical production from $Fe^{II}$ from compounds used as precursors of B, $B_1$ or C=—$T_C$—Y—H.

0.1 ml aliquots of $10^{-4}$ M methanolic solutions of 4-thiazolidin carboxylic aced and 2-oxo-4-thiazolidin carboxylic acid are added to test tubes containing an aqueous solution formed by mixing 0.2 ml of 2 mM desoxyribose, 0.4 ml of buffer phosphate pH 7.4 100 mM and 0.1 ml of 1 mM $Fe^{II}$ $(NH_4)_2(SO_4)_2$ in 2 mM HCl. The test tubes are then kept at a temperature of 37° C. for one hour. Then in each test tube 0.5 ml of a 2.8% solution in trichloroacetic acid in water and 0.5 ml of an aqueous solution 0.1 M thiobarbituric acid are added in the order. A reference blank is constituted by substituting the above 0.1 ml aliquots of the test compound methanolic solutions with 0.1 ml of methanol. The test tubes are closed and heated in an oil bath at 100° C. for 15 minutes. A pink coloration develops the intensity of which is proportional to the quantity of desoxyribose undergone to radical oxidative degradation. The solutions are cooled at room temperature and their absorbances at 532 nm are read against the blank.

The inhibition induced by the precursor of B or $B_1$ or C=—$T_C$—Y—H (wherein the free valence is saturated as above defined) with respect to radical production from $Fe^{II}$ is determined as a percentage by means of the following formula:

$$(1-A_S/A_C) \times 100$$

wherein $A_S$ and $A_C$ are respectively the absorbance values of the solution containing the tested compound+the iron salt and that of the solution containing only the iron salt.

The results are reported in Table IV, which shows that both acids meet test 5 since they inhibit radical production from $Fe^{II}$ in a percentage higher than 50%. Therefore both 4-thiazolidin carboxylic acid and 2-oxo-4-thiazolidin carboxylic acid can be used as precursors of B, $B_1$ or C=—$T_C$—Y—H for obtaining compounds of the present invention.

Example F4

Example F1 was repeated with three groups of rats (each group of of ten animals), one control group not receiving L-NAME and two groups receiving L-NAME, and i.p. administered as it follows:

a. control group (not receiving L-NAME): the carrier (physiologic solution),
b. 1st group receiving L-NAME (group b—comparative administered at the same time with 25 mg/Kg (0.064 mmoles/Kg) of dexamethasone+10.4 mg/Kg (0.064 mmoles/Kg) of N-acetylcysteine in the same above carrier,
c. 2nd group receiving L-NAME (group c) administered with 42.5 mg/Kg (0.064 mmoles/Kg) of the dexamethasone derivative according to the invention (ref. ex. 5) in the same above carrier.

In this experiment vascular tolerability, i.e. the rise in blood pressure (vascular damage) was determined in the animals of groups b and c and expressed as percentages to that of the control group a, assumed to be 100%.

The results are reported in Table V and show that the mixture administered to group b (comparative) induced in the animals an higher blood pressure increase than the compound of the invention (group c).

Example F5

Example F1 was repeated with three groups of rats (each group of of ten animals), one control group not receiving L-NAME and two groups receiving L-NAME, and i.p. administered as it follows:

a. control group (not receiving L-NAME): the carrier (physiologic solution),
b. 1st group receiving L-NAME (group d—comparative administered at the same time with 100 mg/Kg (0.25 mmoles/Kg) of ursodesoxycholic acid+49.5 mg/Kg (0.25 mmoles/Kg) of ferulic acid in the same above carrier,
c. 2nd group receiving L-NAME (group e) administered with 175 mg/Kg (C.25 mmoles/Kg) of the ursodesoxycholic derivative according to the invention (ref. ex. 1) in the same above carrier.

In this experiment hepatic tolerability, i.e. the rise in GPT (hepatic damage) was determined in the animals of groups d and e and expressed as percentages to that of the control group a, assumed to be 100%.

The results are reported in Table VI and show that the mixture administered to group d (comparative), induced in the animals an higher GPT increase than the compound of the invention (group e).

TABLE I

Study of vascular tolerability of hydrocortisone, dexamethasone and prednisolone, and of the corresponding derivatives according to the invention, in animals (rats) both not treated and treated with L-NAME. Vascular tolerability is indicated as % variation of the blood pressure (hypertension) with respect to the controls not treated with L-NAME and treated with the only carrier (physiological solution)

| Compound | Animals non treated with L-NAME | | Animals treated with L-NAME | |
|---|---|---|---|---|
| | dose mg/Kg i.p. | Blood pressure variation % | dose mg/Kg i.p. | Blood pressure variation % |
| carrier | — | 100 | — | 140 |
| hydrocortisone | 10 | 115 | 5 | 160 |
| hydrocortisone der. Ex. 4 | 10 | 98 | 5 | 120 |
| dexamethasone | 5 | 125 | 25 | 170 |
| dexamethasone der. Ex. 5 | 5 | 103 | 25 | 125 |

TABLE I-continued

Study of vascular tolerability of hydrocortisone, dexamethasone and prednisolone, and of the corresponding derivatives according to the invention, in animals (rats) both not treated and treated with L-NAME. Vascular tolerability is indicated as % variation of the blood pressure (hypertension) with respect to the controls not treated with L-NAME and treated with the only carrier (physiological solution)

| Compound | Animals non treated with L-NAME | | Animals treated with L-NAME | |
|---|---|---|---|---|
| | dose mg/Kg i.p. | Blood pressure variation % | dose mg/Kg i.p. | Blood pressure variation % |
| prednisolone | 10 | 119 | 15 | 165 |
| prednisolone der. Ex. 3 | 10 | 102 | 15 | 110 |

TABLE II

Study of hepatic damage, determined by GPT assay, of chenodeoxycholic acid and ursodesoxycholic acid, and of the corresponding derivatives according to the invention, in animals (rats) both not treated and treated with L-NAME. The % variation of GPT with respect to the controls not treated with L-NAME and treated with the only carrier (physiological solution)

| Compound | animals non treated with L-NAME | | Animals treated with L-NAME | |
|---|---|---|---|---|
| | dose mg/kg i.p. | GPT var. % | dose mg/kg i.p. | GPT var. % |
| carrier | — | 100 | — | 230 |
| chenodeoxycholic acid | 100 | 150 | 100 | 350 |
| chenodeoxycholic acid der. Ex. 2 | 100 | 105 | 100 | 130 |
| ursodesoxycholic acid | 100 | 130 | 100 | 276 |
| ursodesoxycholic acid der. Ex. 1 | 100 | 103 | 100 | 123 |

TABLE III

Test 4: Screening of the effectiveness of some substances to inhibit radical production from DPPH.

| Compound | % inhibition radical production from DPPH |
|---|---|
| Solvent | 0 |
| N-acetylcysteine | 100 |
| Cysteine | 100 |
| Ferulic acid | 100 |
| (L)-carnosine | 80 |
| Gentisic acid | 80 |
| 2-oxo-4-thiazolidin carboxylic acid | 0 |
| 4-thiazolidin carboxylic acid | 0 |

TABLE IV

Test 5: study on the effectiveness of the listed substances to inhibit radical production induced by $Fe^{II}$

| Compound | % Radical Inhibition from $Fe^{II}$ |
|---|---|
| White | 0 |
| 2-oxo-4-thiazolidin carboxylic acid | 100 |
| 4-thiazolidin carboxylic acid | 100 |

TABLE V

Study of vascular tolerability in animals (rats) treated with L-NAME and i.p. administered with a mixture of dexamethasone + N-acetylcysteine and with the derivative of dexamethasone of ex. 5 according to the invention. Vascular tolerability is indicated as % variation of the blood pressure (hypertension) with respect to the controls not treated with L-NAME and treated with the only carrier.

| Compound | dose mg/Kg i.p. | Blood pressure variation % |
|---|---|---|
| controls | — | 100 |
| group b - comparative dexamethasone (A) + N-acetyl cysteine (B) | 25(A) + 10.4 (B) | 170 |
| group c dexamethasone der. Ex. 5 | 42.5 | 125 |

TABLE VI

Study of hepatic tolerability in animals (rats) treated with L-NAME and i.p. administered with a mixture of ursodesoxycholic acid + ferulic acid and with the derivative of ursodesoxycholic acid of ex. 1 according to the invention. Hepatic damage is indicated as % variation of GPT with respect to the controls not treated with L-NAME and treated with the only carrier.

| Compound | dose mg/Kg i.p. | GPT variation % |
|---|---|---|
| controls | — | 100 |
| group d - comparative ursodesoxycholic acid (C) + ferulic acid (D) | 100(C) + 49.5(D) | 180 |
| group e ursodesoxycholic acid der. ex. 1 | 175 | 123 |

What is claimed is:

1. A steroidal compound or a salt thereof having the following general formula:

$$A\text{—}B\text{—}T_c\text{—}Y\text{—}NO_2 \quad (I)$$

wherein:
A=R—, wherein R is a steroidal drug radical as defined hereunder,
B=—$T_B$—$X_2$—$T_{BI}$— wherein
  $T_B$ is (CO);
  $T_{BI}$ is S, NH;
  $X_2$ is a bivalent bridging group such that the corresponding precursor of B, having the formula Z—$T_B$—$X_2$—$T_{BI}$—Z' in which Z and Z' are independently H or OH, is selected from the following compounds:

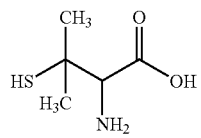
(CV)

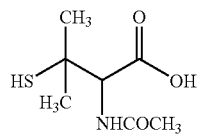
(CVI)

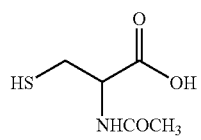
(CVIII)

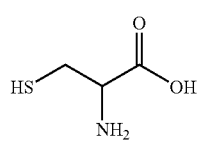
(CVII)

$T_c$ is (CO);
Y has the following meanings:
  a linear or branched $C_1$ to $C_{20}$ alkylenoxy group or a cycloalkylene having from 5 to 7 carbon atoms, in the cycloalkylenic ring one or more carbon atoms can be substituted by heteroatoms, the ring can have side chains of R' type, R' being a linear or branched $C_1$ to $C_{20}$ alkyl; or

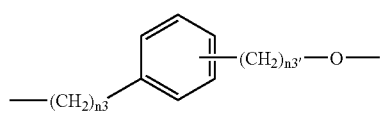

wherein $n3$ is an integer from 0 to 3 and n3' is an integer from 1 to 3,

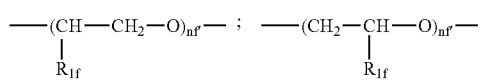

wherein $R_{1f}$=H, $CH_3$ and nf' is an integer from 1 to 6;
R has the following formula:

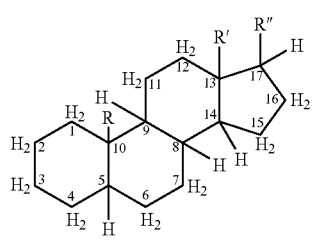

wherein
in substitution of the hydrogen atom of the CH groups or of the two hydrogen atoms of the $CH_2$ groups mentioned in the general formula, the following substituents can be present:

in position 1–2: there may be a double bond;
in position 3: there may be C=O, —OH;
in position 4–5: there may be a double bond;
in position 6: there may be —Cl, —F, —$CH_3$;
in position 7: there may be —Cl, —OH;
in position 9: there may be —Cl, —F;
in position 11: there may be —OH, C=O, —Cl, —$CH_3$;
in position 16: there may be —$CH_3$, —OH;
in position 17: there may be —OH, —$CH_3$;
in position 16–17: there may be the following groups:

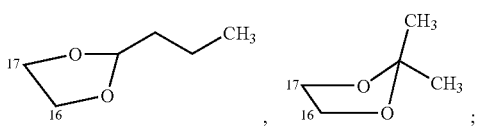

R''' and R', equal or different from each other, are hydrogen or $CH_3$; and
R'' is C(O)$CH_2$O—.

2. The steroidal compound or salt thereof according to claim 1 wherein the steroidal drug radical is derived from one of the following: Budesonide, Hydrocortisone, Beclomethasone, Betamethasone, Chloroprednisone, Clocortolone, Cortisone, Corticosterone, Desonide, Desoximethasone, Dexamethasone, Diflucortolone, Flumethasone, Flunisolide, Fluprednisolone, Flurandrenolide, Meprednisone, Methylprednisolone, Paramethasone, Prednisolone, Prednisone, or Triamcinolone.

3. The steroidal compound or salt thereof according to claim 1 or 2 wherein the precursor of B is

(CVIII)

4. The steroidal compound or salt thereof according to claim 1 wherein Y is a linear or branched $C_1$ to $C_6$ alkylenoxy group.

5. The steroidal compounds or salts thereof according to claim 1 selected from the group consisting of:
  (11β)-11-17-dihydroxy-21-[N-acetyl-S-(4-nitroxybutyroyl) cisteinyloxy]pregne-1,4-diene-3,20-dione;
  (11β)-11-17-dihydroxy-21-[N-acetyl-S-(4-nitroxybutyroyl) cisteinyloxy]pregne-4-ene-3,20-dione; and
  (11β, 16α)-9-fluoro-11-17-dihydroxy-21-[N-acetyl-S-(4-nitroxybutyroyl)cisteinyloxy]-16-methylpregne-1,4-diene-3,20-dione.

6. A method for the treatment of oxidative stress and/or endothelial dysfunctions comprising administering the steroidal compound or salt thereof according to claim 1.

7. A method for the treatment of inflammation comprising administering the steroidal compound or salt thereof according to claim 1.

8. A pharmaceutical formulation comprising the steroidal compound or salt thereof according to claim 1 and a pharmaceutical acceptable carrier.

* * * * *